US005648599A

United States Patent [19]

Tanksley et al.

[11] Patent Number: 5,648,599

[45] Date of Patent: Jul. 15, 1997

[54] GENE CONFERRING DISEASE RESISTANCE TO PLANTS BY RESPONDING TO AN AVIRULENCE GENE IN PLANT PATHOGENS

[75] Inventors: Steven D. Tanksley, Newfield, N.Y.; Gregory B. Martin, West Lafayette, Ind.

[73] Assignee: Cornell Research Foundation, Inc., Ithaca, N.Y.

[21] Appl. No.: 447,185

[22] Filed: May 22, 1995

Related U.S. Application Data

[63] Continuation of Ser. No. 111,078, Aug. 24, 1993, abandoned.

[51] Int. Cl.[6] .............................. A01H 5/00; C12N 5/04; C12N 15/29; C12N 15/54

[52] U.S. Cl. ................................. 800/205; 800/DIG. 13; 800/DIG. 15; 800/DIG. 16; 800/DIG. 18; 800/DIG. 19; 800/DIG. 20; 800/DIG. 21; 800/DIG. 23; 800/DIG. 25; 800/DIG. 46; 800/DIG. 30; 800/DIG. 31; 800/DIG. 42; 800/DIG. 43; 800/DIG. 44; 800/DIG. 55; 435/69.1; 435/415; 435/70.1; 435/417; 435/172.3; 435/194; 435/414; 435/418; 435/419; 435/252.3; 435/320.1; 435/411; 435/412; 536/23.2; 536/23.6

[58] Field of Search ................................. 536/23.2, 23.6; 435/69.1, 70.1, 172.3, 194, 240.4, 252.3, 320.1; 800/205, DIG. 13, 15, 16, 18–21, 23, 25, 26, 30–35, 37, 40–44, 46, 55–60

[56] References Cited

PUBLICATIONS

H.H. Flor, "Host–Parasite Interactions in Flax–Rust—Its Genetic and Other Implications," *Phytopath*, 45:680–685 (1947).

H.H. Flor, "Current Status of the Gene–for–Gene Concept," *Ann. Rev. Phytopath*, 9:275–96 (1971).

B. Staskawicz, et al., "Cloned Avirulence Gene of *Pseudomonas syringae* pv. *glycinea* Determines Race–Specific Incompatibility on Glycine max L., Merr." *Proc. Natl. Acad. Sci USA*, 81:6024–28 (1984).

A.H. Ellingboe, "Genetics of Host–Parasite Interactions," *Encyclopedia of Plant Pathology, New Series, vol. 4: Physiological Plant Pathology*, pp. 761–78 (1976).

D.W. Gabriel et al. "Gene–for–Gene Interactions of Five Cloned Avirulence Genes from *Xanthomonas campestris* pv *malvacearum* Specific Resistance Genes in Cotton," *Proc. Natl. Acad. USA* 83:6415–19 (1986).

S.H. Hulbert, et al., "Recombination at the Rp1 Locus of Maize," *Mol. Gen. Genet.*, 226:377–82.

N.T. Keen, et al., "New Disease Resistance Genes in Soybean Against *Pseudomonas syringae* pv. *glycinea*: Evidence That One of Them Interacts with a Bacterial Elicitor," *Theor. Appl. Genet.* 81:133–38 (1991).

R. Messeguer, et al., "High Resolution RFLP Map Around the Root–knot Nematode Resistance Gene (Mi) in Tomato," *Theor. Appl. Genet* 82:529–36 (1991).

T. Debener, et al., "Identification and Molecular Mapping of a Single *Arabidopsis thaliana* locus Determining Resistance to a Phytopathogenic *Pseudomonas syringae* isolate," *Plant J.* 1:289–302 (1991).

D.Y. Kobayashi, et al. "Cloned Avirulence Genes from Tomato Pathogen *Pseudomonas syringae* pv. tomato Confer Cultivar Specificity on Soybean," *Proc. Natl. Acad. Sci.* USA 86:157–61 (1989).

J.A.L. Van Kan, et al., "Cloning and Characterization of cDNA of Avirulence Gene avr9 of the Fungal Pathogen *Cladosporium falvum* Casual Agent of Tomato Leaf Mold," *Mol. Plant–Microbe Interactions* 4:52–59 (1991).

J.L. Bennetzen et al., "Approaches and Progress in the Molecular Cloning of Plant Disease Resistance Genes," *Genetic Engineering*, 14:99–124 (1992).

G. Felix, et al., "Rapid Changes of Protein Phosphorylation are Involved in Transduction of the Elicitor Signal in Plant Cells," *Proc. Natl. Acad. Sci. USA*, 88:8831–34 (1991).

V. Raz, et al., "Ethylene Signal is Transduced via Protein Phosphorylation Events in Plants," *The Plant Cell*, 5:523–30 (1993).

E.E. Farmer, et al., "Oligouronide–Enhanced Plasma Membrane Protein Phosphorylation," *J. Biological Chemistry*, 266:3140–45.

G.B. Martin, et al., "Rapid Identification of Markers Linked to Pseudomonas Resistance Gene in Tomato Using Random Primers Near–isogeneic Lines," *Proc. Natl. Acad. Sci. USA*, 88:2336–40 (1991).

G.B. Martin, et al., "High Resolution Linkage Analysis and Physical Characterization of the Pto Bacterial Resistance in Tomato," *Molecular Plant Microbe Interaction*, 6:21–34 (1993).

G.B. Martin, et al., "Towards Positional Cloning of the Pto Bacterial Resistance Locus From Tomato," *Advances in Molecular Genetics of Plant–Microbe Interactions*, pp. 451–55 (1993).

R.E. Pitblado et al., "Genetics Basis of Resistance to *Pseudomonas syringae* pv. tomato in Field Tomatoes," *Can. J. Plant Path.*, 5:251–55 (1983).

Song et al. 1995. Science 270:1804–1806.

Goring et al. 1992. The Plant Cell 4:1273–1281.

Stein et al. 1991 Proc. Natl. Acad. Sci. USA 88:8816–8820.

Martin et al. 1992 Mol. Gen. Genet. 233(1):25–32.

Rommens et al. 1989. Science 245:1059–1065.

Bidwai et al. 1987. Proc. Natl. Acad. Sci. USA 84:6755–9.

Nelson et al. 1988. Bio/Technology 6(4):403–409.

*Primary Examiner*—David T. Fox

*Attorney, Agent, or Firm*—Nixon, Hargrave, Devans & Doyle

[57] ABSTRACT

The present invention relates to an isolated gene fragment which confers disease resistance to plants by responding to an avirulence gene in plant pathogens. The gene fragment encodes for protein kinase, particularly serine/threonine kinase. The gene can be cloned into an expression vector to produce a recombinant DNA expression system suitable for insertion into cells to form a transgenic plant transformed with that gene fragment. Also disclosed is a process of conferring disease resistance to plants by growing plant host cells transformed with that expression system and expressing the gene conferring disease resistance to impart such resistance to the host cells.

29 Claims, 12 Drawing Sheets

MAP OF LAMBDA GT10 VECTOR

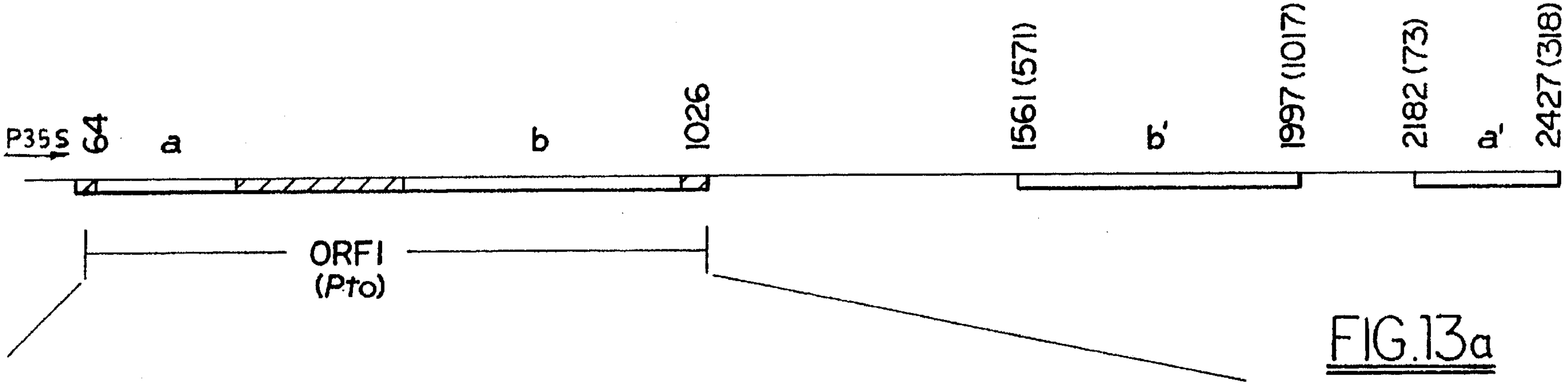

FIG.13a

| | | | | | | |
|---|---|---|---|---|---|---|
| | | | | (I) | | |
| MGSKYSKATN | SINDALSSSY | LVPFESYRVP | LVDLEEATNN | FDHKFLIGHG | VFGKVYKGVL | 60 |
| (II) | | (III) | (IV) | | (V) | |
| RDGAKVALKR | RTPESSQGIE | EFETEIETLS | FCRHPHLVSL | IGFCDERNEM | ILIYKYMENG | 120 |
| | | | | (VIb) | | |
| NLKRHLYGSD | LPTMSMSWEQ | RLEICIGAAR | GLHTLHTRAI | IHRDVKSINI | LLDENFVPKI | 180 |
| (VII) | | (VIII) | | (IX) | | |
| TDFGISKKGT | ELDQTHLSTV | VKGTLGYIDP | EYFIKGRLTE | KSDVYSFGVV | LFEVLCARSA | 240 |
| | (X) | | | | (XI) | |
| IVQSLPREMV | NLAEWAVESH | NNGQLEQIVD | PNLADKIRPE | SLRKFGDTAV | KCLALSSEDR | 300 |
| PSMGDVLWKL | EYALRLQESV | I | | | | 321 |

FIG.13b

GENE CONFERRING DISEASE RESISTANCE TO PLANTS BY RESPONDING TO AN AVIRULENCE GENE IN PLANT PATHOGENS

This invention arose out of research sponsored by NSF (Grant No. DMB-89-05997) and USDA/NRI (Grant No. 91-37300-6418).

This application is a continuation of application Ser. No. 08/111,078, filed Aug. 24, 1993, now abandoned.

FIELD OF THE INVENTION

The present invention relates to a gene conferring disease resistance to plants by responding to an avirulence gene in plant pathogens.

BACKGROUND OF THE INVENTION

Plants can be damaged by a wide variety of pathogenic organisms including viruses, bacteria, fungi and nematodes. Annual crop losses due to these pathogens is in the billions of dollars. Synthetic pesticides represent one form of defense against pathogens, and each year thousands of tons of such chemicals are applied to farm land and agricultural commodities. The cost of chemical pesticides is measured not only in the cost of producing these pesticides but also in both short term and long term environmental damage and the inherent risks to human health.

Plants also contain their own innate mechanisms of defense against pathogenic organisms. Natural variation for resistance to plant pathogens has been identified by plant breeders and pathologists and bred into many crop plants. These natural disease resistance genes often provide high levels of resistance (or immunity) to pathogens and represent the most economical and environmentally friendly form of crop protection. Despite the commercial significance, little is known about the molecular basis of natural disease resistance.

It has been postulated that disease resistance may be induced by the interaction of single genes in both the pathogen and the plant host. See A. H. Flor, "Host-Parasite Interactions in Flat-Rust—its Genetics and Other Implications," *Phytopath,* 45:680–685 (1947) and A. H. Flor, "Current Status of the Gene-for-Gene Concept," *Ann. Rev. Phytopath,* 9:275–96 (1971), both of which are hereby incorporated by reference. Many plant disease resistance genes have been mapped to single loci, and individual avirulence genes have been isolated from bacterial and fungal pathogens. See B. Staskawicz, et al., "Cloned Avirulence Gene of *Pseudomonas syringae* pv. glycinea Determines Race-Specific Incompatibility on Glycine max Lo, Merr." *Proc. Natl. Acad. Sci USA,"* 81:6024–28 (1984); A. M. Ellingboe, "Genetics of Host-Parasite Interactions," Encyclopedia of Plant Pathology, New Series, Vol. 4*: Physiological Plant Pathology*, pp. 761–78 (1976); D. W. Gabriel et al. "Gene-for-Gene Interactions of Five Cloned Avirulence Genes from *Xanthomonas campestris* pv malvacearum with Specific Resistance Genes in Cotton," *Proc Natl Acad Sci USA* 83:6415–19 (1986); S. H. Hulbert, et al., "Recombination at the Rp1 Locus of Maize," *Mol. Gen. Genet.*, 226:377–82 (1991); N. T. Keen, et al., "New Disease Resistance Genes in Soybean Against *Pseudomonas syringae* pv. glycinea: Evidence That One of Them Interacts with a Bacterial Elicitor," *Theor. Appl. Genet.* 81:133–38 (1991); R. Messeguer et al., "High Resolution RFLP Map Around the Root-knot Nematode Resistance Gene (Mi) in Tomato," *Theor. Appl. Genet* 82:529–3G (1991); T. Debener, et al., "Identification and Molecular Mapping of a Single *Arabidopsis thaliana* locus Determining Resistance to a Phytopathogenic Pseudomonas syringae isolate," Plant J 1:289:302 (1991); D. Y. Kobayashi, et al. "Cloned Avirulence Genes from Tomato Pathogen *Pseudomonas syringae* pv. tomato Confer Cultivar Specificity on Soybean," *Proc. Natl. Acad. Sci. USA* 86:157–61 (1989); and J. A. L. Van Kan, et al., "Cloning and Characterization of cDNA of Avirulence Gene avr9 of the Fungal Pathogen *Cladosporium fulvum*, Causal Agent of Tomato Leaf Mold," *Mol. Plant-Microbe Interactions* 4:52–59 (1991), all of which are hereby incorporated by reference. However, despite this progress, the molecular isolation of plant disease resistance genes has been hindered by the fact that little is known of the gene products encoded at these loci.

The phenomenon of disease resistance is believed to be initiated by physical contact between a pathogen and a potentially compatible portion of the host. Once such contact has occurred, usually as a result of wind or rain vectored deposition of the pathogen, the pathogen must recognize that such contact has been established in order to initiate the pathogenic process. Likewise, such recognition by the host is required in order to initiate a resistance response. The precise manner in which such recognition occurs is not clear. However, pathogen recognition is believed to be associated with low pH of plant tissues or the presence of plant-specific metabolites. On the other hand, recognition by the host involves at least two partly separate pathways of recognition. A general mechanism detects a presence of the cell wall fragments from the pathogen and/or the damaged host. In addition, recognition results from a race-specific mechanism where the host disease resistance gene recognizes the avirulence gene of the pathogen. Both host recognition mechanisms lead to one or more levels of gene activation which in turn lead to production of defensive resistance factors (e.g., gum or cork production, production of inhibitors of pathogen proteases, deposition of lignin and hydroxyproplin-rich proteins in cell walls) and offensive resistance factors (e.g., production of phytoalexins, secreted chitinases). If the rate and level of activation of the genes producing these factors is sufficiently high, the host is able to gain an advantage on the pathogen. On the other hand, if the pathogen is fully activated at an earlier stage in the infection process, it may overwhelm both the offensive and defensive resistance factors of the plant. The phenomenon of disease resistance is fully discussed in J. L. Bennetzen et al., "Approaches and Progress in the Molecular Cloning of Plant Disease Resistance Genes," *Genetic Engineering,* 14:99–124 (1992), which is hereby incorporated by reference.

Recently, elicitors of plant defense responses have been shown to induce phosphorylation and dephosphorylation of specific plant proteins, and inhibitors of mammalian protein kinases were found to inhibit expression of certain plant defense genes. See G. Felix, et al., "Rapid Changes of Protein Phosphorylation are Involved in Transduction of the Elicitor Signal in Plant Cells," *Proc. Natl. Acad. Sci. USA,* 88:8831–34 (1991); V. Raz, et al., "Ethylene Signal is Transduced via Protein Phosphorylation Events in Plants," *The Plant Cell,* 5:523–30 (1993); and E. E. Farmer, et al. "Oligosaccharide Signaling in Plants—Specificity of Oligouronide-Enhanced Plasma Membrane Protein Phosphorylation," *J. Biological Chemistry,* 266:3140–45 (1991), all of which are hereby incorporated by reference. At best, these references suggest that kinases are present in the metabolic pathway of disease resistance. These publications, however, do not disclose a gene which confers disease resistance to plants by responding to an avirulence gene in plant pathogens.

In tomato, resistance to the bacterial pathogen *Pseudomonas syringae* pv. tomato is encoded by a single locus (Pto) that displays dominant gene action. See R. E. Pitbaldo et al., "Genetic Basis of Resistance to *Pseudomonas syringae* pv. tomato in Field Tomatoes," *Can. J. Plant Path.,* 5:251–55 (1983) ("Pitbaldo 1983"), which is hereby incorporated by reference. As with many commercially important traits in cultivated tomato (*Lycopersicon esculentum*), the resistance was identified in a wild tomato species, specifically *Lycopersicon pimpinellifolium.* See Pitbaldo 1983. Since the Pto gene was introgressed into tomato from a wild species, the region around the locus is polymorphic with respect to *L. esculentum* DNA. This polymorphism has been exploited by using a strategy relying on near-isogenic lines to identify molecular markers closely linked to Pto. See G. B. Martin, et al., "Rapid Identification of Markers Linked to Pseudomonas Resistance Gene in Tomato Using Random Primers and Near-isogenic Lines," *Proc. Natl. Acad. Sci. USA,* 88:2336–40 (1991) ("Martin et. al. 1991"), which is hereby incorporated by reference. Significant effort has been undertaken to map genetically the Pto gene. See G. B. Martin, et al. "High Resolution Linkage Analysis and Physical Characterization of the Pto Bacterial Resistance in Tomato," *Molecular Plant Microbe Interaction,* 6:21–34 (1993) ("Martin et. al. 1993") and G. B. Martin, et al, "Towards Positional Cloning of the Pto Bacterial Resistance Locus From Tomato," *Advances in Molecular Genetics of Plant-Microbe Interactions*, pp. 451–55 (1993). Moreover, the Pto gene is present in a number of commercial tomato varieties where it provides complete protection against *Pseudomonas syringae* pv. tomato bacteria and the disease referred to as "bacterial specks". Despite its wide-spread commercial use, no one has cloned or molecularly analyzed/characterized the Pto gene from tomato or a related disease resistance gene from any other plant species.

SUMMARY OF THE INVENTION

The present invention relates to an isolated gene fragment which confers disease resistance to plants by responding to an avirulence gene in plant pathogens. It has been found that the gene fragment encodes for a protein kinase, more particularly a serine/threonine kinase. This gene can be inserted into an expression vector to produce a recombinant DNA expression system which forms another aspect to the present invention.

In another aspect of the present invention, a heterologous DNA conferring disease resistance to plants by responding to an avirulence gene in plant pathogens can be used to transform cells from transgenic plants. Again, the gene fragment encodes for protein kinase, particularly serine/threonine kinase. A process of conferring disease resistance to plants by growing plant host cells transformed with a recombinant DNA expression system comprising an expression vector into which this heterologous DNA is inserted and then expressing the heterologous DNA in the host cells to confer disease resistance is also disclosed.

In yet another aspect of the present invention, an isolated protein is disclosed which confers disease resistance to plants. That protein comprises an amino acid sequence for protein kinase, particularly serine/threonine kinase.

BRIEF DESCRIPTION OF THE DRAWINGS

FIG. 13A is a map of the CD186 cDNA insert, indicating the position and orientation of ORF1 (Pto) and 35S CaMV promoter on pPTC8.

FIG. 13B is the deduced amino acid sequence for ORF1 (Pto) shown in standard 1-letter code.

DETAILED DESCRIPTION OF THE INVENTION

Figure 1:
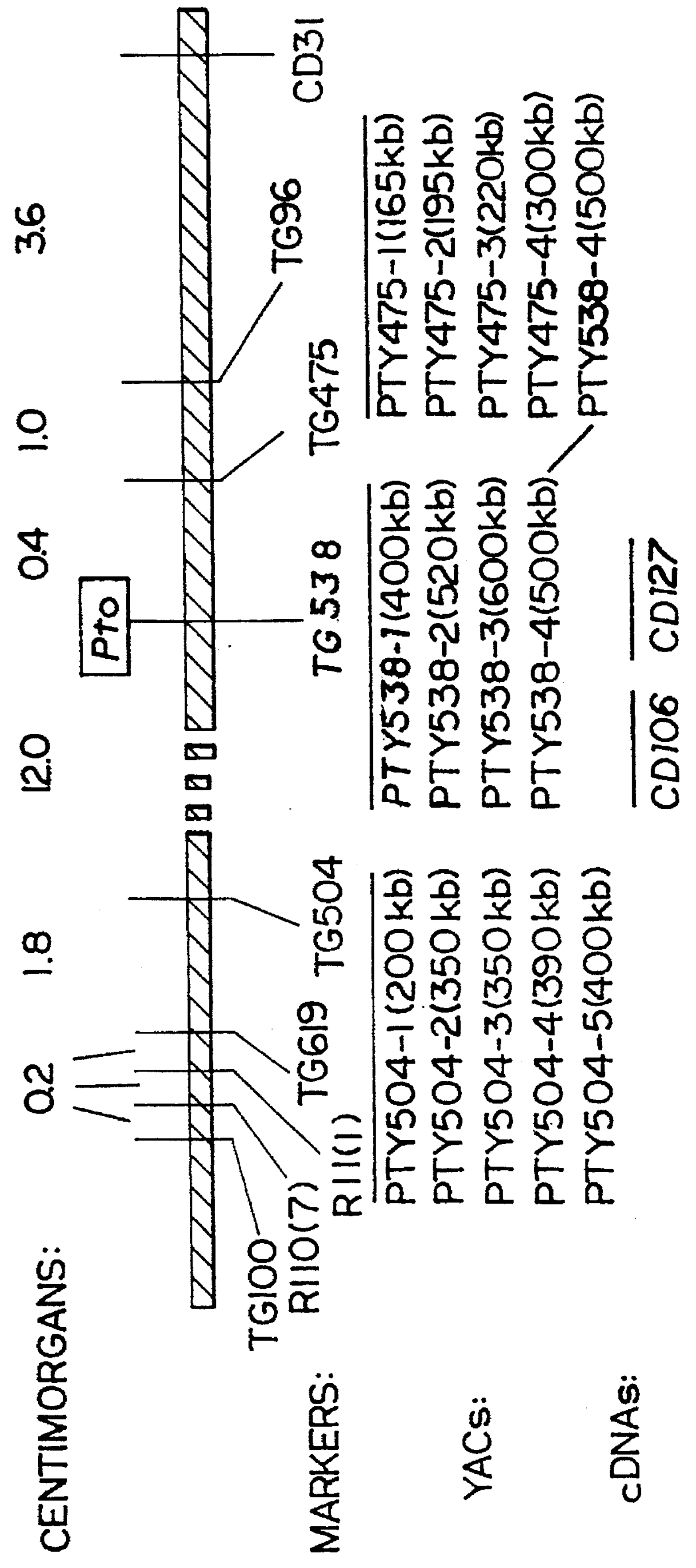
FIG. 1 is a linkage map of a 20 cM (i.e. centimorgan) region of tomato chromosome 5 developed from an $F_2$ population segregating for Pto. This figure also shows the YAC clones identified with TG504, TG538, and TG475 as well as the 2 cDNAs identified by PTY 538-1. Additional markers at some loci are in parentheses.

The present invention relates to an isolated gene fragment conferring disease resistance to plants by responding to an avirulence gene in plant pathogens. The gene fragment encodes for protein kinase, particularly serine/threonine kinase. An amino acid sequence encoded by the gene fragment is SEQ. ID. No. 1 as follows:

| | | | | | | | | | | | | | | | |
|---|---|---|---|---|---|---|---|---|---|---|---|---|---|---|---|
| Met | Gly | Ser | Lys | Tyr | Ser | Lys | Ala | Thr | Asn | Ser | Ile | Asn | Asp | Ala | Leu |
| 1 | | | | 5 | | | | | 10 | | | | | 15 | |
| Ser | Ser | Ser | Tyr | Leu | Val | Pro | Phe | Glu | Ser | Tyr | Arg | Val | Pro | Leu | Val |
| | | | 20 | | | | | 25 | | | | | 30 | | |
| Asp | Leu | Glu | Glu | Ala | Thr | Asn | Asn | Phe | Asp | His | Lys | Phe | Leu | Ile | Gly |
| | | 35 | | | | | 40 | | | | | 45 | | | |
| His | Gly | Val | Phe | Gly | Lys | Val | Tyr | Lys | Gly | Val | Leu | Arg | Asp | Gly | Ala |
| | 50 | | | | | 55 | | | | | 60 | | | | |
| Lys | Val | Ala | Leu | Lys | Arg | Arg | Thr | Pro | Glu | Ser | Ser | Gln | Gly | Ile | Glu |
| 65 | | | | | 70 | | | | | 75 | | | | | 80 |
| Glu | Phe | Glu | Thr | Glu | Ile | Glu | Thr | Leu | Ser | Phe | Cys | Arg | His | Pro | His |
| | | | | 85 | | | | | 90 | | | | | 95 | |
| Leu | Val | Ser | Leu | Ile | Gly | Phe | Cys | Asp | Glu | Arg | Asn | Glu | Met | Ile | Leu |
| | | | 100 | | | | | 105 | | | | | 110 | | |
| Ile | Tyr | Lys | Tyr | Met | Glu | Asn | Gly | Asn | Leu | Lys | Arg | His | Leu | Tyr | Gly |
| | | 115 | | | | | 120 | | | | | 125 | | | |
| Ser | Asp | Leu | Pro | Thr | Met | Ser | Met | Ser | Trp | Glu | Gln | Arg | Leu | Glu | Ile |
| | 130 | | | | | 135 | | | | | 140 | | | | |
| Cys | Ile | Gly | Ala | Ala | Arg | Gly | Leu | His | Tyr | Leu | His | Thr | Arg | Ala | Ile |
| 145 | | | | | 150 | | | | | 155 | | | | | 160 |
| Ile | His | Arg | Asp | Val | Lys | Ser | Ile | Asn | Ile | Leu | Leu | Asp | Glu | Asp | Phe |
| | | | | 165 | | | | | 170 | | | | | 175 | |
| Val | Pro | Lys | Ile | Thr | Asp | Phe | Gly | Ile | Ser | Lys | Lys | Gly | Thr | Glu | Leu |
| | | | 180 | | | | | 185 | | | | | 190 | | |
| Asp | Gln | Thr | His | Leu | Ser | Thr | Val | Val | Lys | Gly | Thr | Leu | Gly | Tyr | Ile |
| | | 195 | | | | | 200 | | | | | 205 | | | |
| Asp | Pro | Glu | Tyr | Phe | Ile | Lys | Gly | Arg | Leu | Thr | Glu | Lys | Ser | Asp | Val |
| | 210 | | | | | 215 | | | | | 220 | | | | |
| Tyr | Ser | Phe | Gly | Val | Val | Leu | Phe | Glu | Val | Leu | Cys | Ala | Arg | Ser | Ala |
| 225 | | | | | 230 | | | | | 235 | | | | | 240 |
| Ile | Val | Gln | Ser | Leu | Pro | Arg | Glu | Met | Val | Asn | Leu | Ala | Glu | Trp | Ala |
| | | | | 245 | | | | | 250 | | | | | 255 | |
| Val | Glu | Ser | His | Asn | Asn | Gly | Gln | Leu | Glu | Gln | Ile | Val | Asp | Pro | Asn |
| | | | 260 | | | | | 265 | | | | | 270 | | |
| Leu | Ala | Asp | Lys | Ile | Arg | Pro | Glu | Ser | Leu | Arg | Lys | Phe | Gly | Asp | Thr |
| | | 275 | | | | | 280 | | | | | 285 | | | |
| Ala | Val | Lys | Cys | Leu | Ala | Leu | Ser | Ser | Glu | Asp | Arg | Pro | Ser | Met | Gly |
| | 290 | | | | | 295 | | | | | 300 | | | | |
| Asp | Val | Leu | Trp | Lys | Leu | Glu | Tyr | Ala | Leu | Arg | Leu | Gln | Glu | Ser | Val |
| 305 | | | | | 310 | | | | | 315 | | | | | 320 |
| Ile | | | | | | | | | | | | | | | |

As demonstrated in the examples infra, a comparison of this sequence with those on available databases indicates that this sequence includes 11 subdomains, including 15 invariant amino acids, characteristic of protein kinases. In addition, there are sequences indicative of serine/theonine kinases.

Preferably, the gene fragment conferring disease resistance has nucleotide sequence SEQ. ID. No. 2 as follows:

ATGGGAAGCAAGTATTCTAAGGCAACAAATTCCATAAATGATGCTTTAAGCTCGAGTTATCTCGT
TCCTTTTGAAAGTTATCGAGTTCCTTTAGTAGATTTGGAGGAAGCAACTAATAATTTTGATCACA
AGTTTTTAATTGGACATGGTGTCTTTGGGAAGGTTTACAAGGGTGTTTTGCGTGATGGAGCAAAG
GTGGCCCTGAAAAGGCGTACACCTGAGTCCTCACAAGGTATTGAAGAGTTCGAAACAGAAATTGA
GACTCTCTCATTTTGCAGACATCCGCATCTGGTTTCATTGATAGGATTCTGTGATGAAAGAAATG
AGATGATTCTAATTTATAAATACATGGAGAATGGGAACCTCAAGAGACATTTGTATGGATCAGAT
CTACCCACAATGAGCATGAGCTGGGAGCAGAGGCTGGAGATATGCATAGGGGCAGCCAGAGGTCT
ACACTACCTTCATACTAGAGCAATTATACATCGTGATGTCAAGTCTATAAACATATTGCTTGATG

-continued

```
AGAATTTTGTGCCAAAAATTACTGATTTTGGAATATCCAAGAAAGGGACTGAGCTTGATCAAACC
CATCTTAGCACAGTAGTGAAAGGAACTCTCGGCTACATTGACCCTGAATATTTTATAAAGGGACG
ACTCACTGAAAATCTGATGTTTATTCTTTCGGTGTTGTTTTTATTCGAAGTTCTTTGTGCTAGGT
CTGCCATAGTTCAATCTCTTCCAAGGGAGATGGTTAATTTAGCTGAATGGGCAGTGGAGTCGCAT
AATAATGGACAGTTGGAACAAATCGTAGATCCCAATCTTGCAGATAAAATAAGACCAGAGTCCCT
CAGGAAGTTTGGAGATACAGCGGTAAAATGCTTAGCTTTGTCTAGTGAAGATAGGCCATCAATGG
GTGATGTGTTGTGGAAACTGGAGTATGCACTTCGTCTCCAAGAGTCTGTTATTTAA
```

Figure 9:
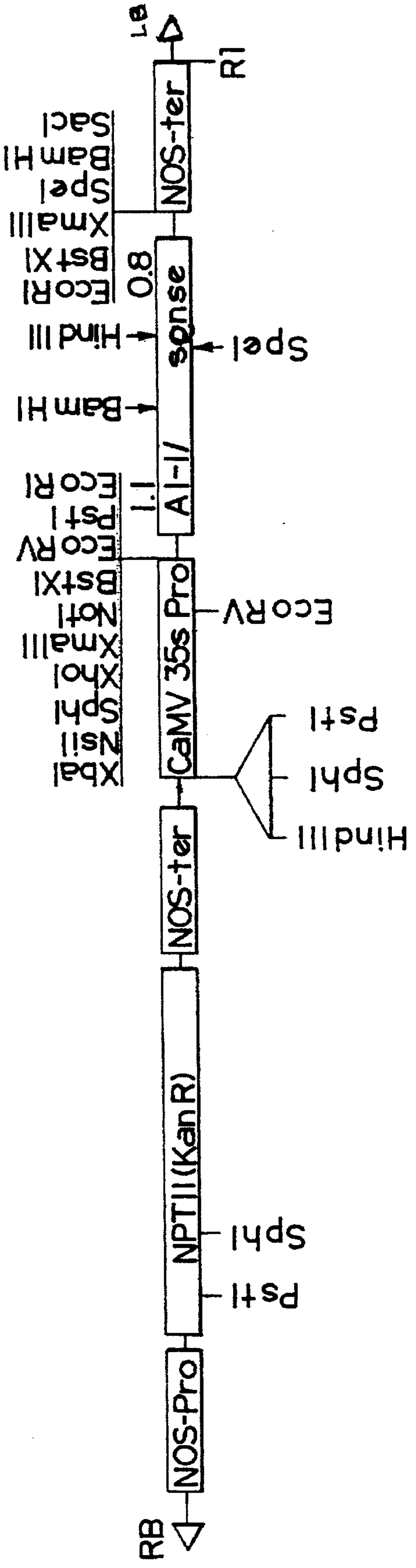
FIG. 9 is a map of the T-DNA region of plasmid vector pPTC8.

The DNA molecule or gene fragment conferring disease resistance to plants by responding to an avirulence gene in plant pathogens can be incorporated in plant or bacterium cells using conventional recombinant DNA technology. Generally, this involves inserting the DNA molecule into an expression system to which the DNA molecule is heterologous (i.e., not normally present). The heterologous DNA molecule is inserted into the expression system or vector in proper orientation and correct reading frame. The vector contains the necessary elements for the transcription and translation of the inserted protein-coding sequences. A large number of vector systems known in the art can be used, such as, plasmids, bacteriophage virus or other modified viruses. Suitable vectors include, but are not limited to the following viral vectors such as lambda vector system λgt11, λgt10, Charon 4, and plasmid vectors such as pBI121, pBR322, pACYC177, pACYC184, pAR series, pKK223-3, pUC8, pUC9, pUC18, pUC19, pLG339, pRK290, pKC37, pKC101, pCDNAII, and other similar systems. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference. The plasmid pBI121 is available from Clontech Laboratories, Palo Alto, Calif., (see FIG. 9) has been used.

In order to obtain efficient expression of the gene or gene fragment of the present invention, a promoter must be present in the expression vector. RNA polymerase normally binds to the promoter and initiates transcription of a gene or a group of linked genes and regulatory elements (operon) in bacteria. Promoters vary in their strength, i.e., ability to promote transcription. Depending upon the host cell system utilized, any one of a number of suitable promoters can be used. Suitable promoters include nos promoter, the small subunit ribulose bisphosphate carboxylase genes, the small subunit chlorophyll A/B binding polypeptide, the 35S promoter of cauliflower mosiac virus, and promoters isolated from plant genes, including the Pto promoter itself. See C. E. Vallejos, et al., "Localization in the Tomato Genome of DNA Restriction Fragments Containing Sequences Homologous to the RRNA (45S), the major chlorophyll A/B Binding Polypeptide and the Ribulose Bisphosphate Carboxylase Genes," *Genetics* 112: 93–105 (1986) which discloses the small subunit materials. The nos promoter and the 35S promoter of cauliflower mosiac virus are well known in the art.

Once the disease resistance gene of the present invention has been cloned into an expression system, it is ready to be transformed into a plant cell. Plant tissue suitable for transformation include leaf tissues, root tissues, meristems, and protoplasts. It is particularly preferred to utilize explants of hypocotyls and cotyledons.

One technique of transforming plants with the gene conferring disease resistance in accordance with the present invention is by contacting the tissue of such plants with an inoculum of a bacteria transformed with a vector comprising a gene in accordance with the present invention which confers disease resistance and encodes for protein kinase. Generally, this procedure involved inoculating the plant tissue with a suspension of bacteria and incubating the tissue for 48 to 72 hours on regeneration medium without antibiotics at 25°–28° C.

Bacteria from the genus Agrobacterium can be utilized to transform plant cells. Suitable species of such bacterium include *Agrobacterium tumefaciens* and *Agrobacterium rhizogenes. Agrobacterium tumefaciens* (e.g., strains LBA4404 or EHA105) is particularly useful due to its well-known ability to transform plants.

Another approach to transforming plant cells with a gene which confers disease resistance and encodes for a protein kinase involves propelling inert or biologically active particles at plant tissues cells. This technique is disclosed in U.S. Pat. Nos. 4,945,050, 5,036,006, and 5,100,792 all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the gene conferring disease resistance and encoding for protein kinase. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

The isolated gene fragment of the present invention or related protein kinase genes can be utilized to confer disease resistance to a wide variety of plant cells, including gymnosperms, monocots, and dicots. Although the gene can be inserted into any plant cell falling within these broad classes, it is particularly useful in crop plant cells, such as rice, wheat, barley, rye, corn, potato, sweet potato, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane. The amino acid sequence identified by SEQ. ID. No. 1, and the nucleotide sequence, identified by SEQ. ID. No. 2, are particularly useful in conferring disease resistance to otherwise disease-prone tomato plants. The present invention may also be used in conjunction with non-crop plants, including *Arabidopsis thaliana.*

The expression system of the present invention can be used to transform virtually any crop plant cell under suitable conditions. Cells transformed in accordance with the present invention can be grown in vitro in a suitable medium to confer disease resistance by producing protein kinases. This protein can then be harvested or recovered by conventional purification techniques. The isolated protein can be applied to plants (e.g., by spraying) as a topical application to impart disease resistance. Alternatively, transformed cells can-be regenerated into whole plants such that this protein imparts disease resistance to the intact transgenic plants. In either case, the plant cells transformed with the recombinant DNA expression system of the present invention are grown and caused to express that DNA in the cells to confer disease resistance on them.

Regardless of whether the DNA molecule of the present invention is expressed in intact plants or in culture, expression of the desired protein follows essentially the same basic mechanism. Specifically, transcription of the DNA molecule is initiated by the binding of RNA polymerase to the DNA molecule's promoter. During transcription, movement of the RNA polymerase along the DNA molecule forms messenger RNA. As a result, the DNA molecule that encodes for the hybrid protein of the present invention is transcribed into the corresponding messenger RNA. This messenger RNA then moves to the ribosomes of the rough endoplasmic reticulum which, with transfer RNA, translates the messenger RNA into the protein conferring disease resistance to plants of the present invention. This protein then proceeds to trigger the plant's disease resistance mechanism. Although the sequence of events involved in the resistance mechanism is not well understood, it is expected that isolation of the gene fragment of the present invention and identification of its sequence will lead to a greater understanding of how disease resistance is conferred.

EXAMPLES

Example 1

Identifying cDNA clones by map-based cloning.

A. High resolution linkage mapping and physical mapping of the Pto region on tomato chromosome 5.

Plant material and segregating populations

An $F_2$ population (86T64) derived from an interspecific cross of Lycopersicon esculentum cv. VF36-Tm2a x *L.pennellii* LA716 was used initially to assign markers to the Pto region. To order the markers with respect to Pto, $F_2$ population (90GM251) derived from a cross between two near-isogenic lines differing for Pst susceptibility was used. Rio Grande-PtoR derives its resistance from *L.pimpinellifolium* and has undergone six backcrosses to Rio Grande and a final selfing generation.

Scoring plant reactions to Fenthion and to *Pseudomonas syringae* pv. tomato

Approximately 100 seeds were sown per flat in the greenhouse (20°–25° C.) in a 1:2:1 (vol/vol) mixture of peat, loam and perlite. Six weeks after germination, the plants were sprayed with a solution of 0.15% Fenthion/0.05% Silwet L-77 dispersed in sterile distilled water (Silwet L-77 source: Union Carbide, Southbury, Conn.); Fenthion source: Mobay Corp., Kansas City, Mo.). After 3–4 days, small necrotic lesions (1–2 mm) were visible on controls known to be either homozygous or heterozygous at the Pto locus. A razor blade was used to cull all $F_2$ seedlings showing the necrotic lesions and one week later the Fenthion treatment and culling was repeated. Those seedlings which remained symptom-free after two Fenthion treatments were placed in the field and scored with flanking RFLP markers to identify plants having crossover events in the Pto region.

$F_3$ progeny from $F_2$ plants having crossovers near the Pto locus were screened for their reaction to *Pseudomonas syringae* pv. tomato (Pst; strain PT11) in the greenhouse as described by Martin et al. (1991), which is hereby incorporated by reference, except that instead of using cotton swabs the plants were dipped in a solution of $10^6$ colony-forming units per ml Pst strain PT11/0.05% Silwet L-77/10 mM $MgCl_2$ dispersed in sterile distilled water. Between 20 and 30 $F_3$ plants were sown as described above and treated at the three-to four-leaf stage. Reaction to the pathogen was scored after 7 days as either susceptible—indicated by numerous necrotic specks surrounded by chlorotic halos—or as resistant—indicated by the absence of necrotic specks on the inoculated leaves.

Pulsed field gel electrophoresis

Preparation of tomato protoplasts (cvs. Rio Grande-PtoR and Rio Grande), isolation of high molecular weight DNA and digestion in agarose blocks was performed as described in M. W. Ganal et. al., "Analysis of Tomato DNA by Pulse Field Gel Electrophoresis," *Plant Mol. Biol. Rep.* 7:17–27 (1989) ("Ganal et. al. 1989"), which is hereby incorporated by reference. CHEF gels (Chu et al, 1986, which is hereby incorporated by reference) were used separate the digested high molecular weight DNA. Gels were prepared in 0.5× TBE (1× TBE=0.089M Tris, 0.089M boric acid, 0.002M EDTA) at an agarose concentration of 1%. For DNA blotting, the gels were treated with UV light (254 nm for 5 minutes using a Fotodyne Transilluminator Model 3-4400) and then blotted onto Hybond N+ (Amersham Co.) using the recommended alkaline (0.4N NaOH) blotting procedure. The molecular weight size standards included lambda concatamers (48.5 kb ladder, FMC Bioproducts, Rockland, Me.) and yeast chromosomes from strain AB1380 (Burke et al. 1987), which is hereby incorporated by reference.

Genetic linkage analysis

A linkage map for a cross between *L.esculentum* and *L.pennelli* was constructed using Mapmaker software on a Sun II workstation as described previously (Lander et al., 1987; Tanksley et al., 1992, which are hereby incorporated by reference). All markers shown placed with a LOD score of >3. The ordering of the markers for the other two populations were determined using Mapmaker and the ripple command gave a ΔLOD of >2.9 for all alternative triple point placements. Recombination frequencies between markers were calculated manually using the maximum likelihood estimators of Allard (1956), which is hereby incorporated by reference.

Identification of markers in the Pto region

Three approaches were used to identify a total of 28 markers, shown below in Table 1, linked to the Pto gene.

TABLE 1

| Marker | Type | Enzyme(s)**** showing RFLP between NILs | Reference, all of which are hereby incorporated by reference |
|---|---|---|---|
| CD31A | cDNA | EV, X | Bernatzky and Tanksley, 1986* |
| CT63A | cDNA | none | Tanksley et al., 1992** |
| CT104A | cDNA | none | Martin et al., 1993 |
| CT155 | cDNA | H | Tanksley et al., 1992 |
| CT201A | cDNA | none | Tanksley et al., 1992 |

TABLE 1-continued

| Marker | Type | Enzyme(s)**** showing RFLP between NILs | Reference, all of which are hereby incorporated by reference |
|---|---|---|---|
| CT202 | cDNA | none | Tanksley et al., 1992 |
| CT260A | cDNA | B, X | Tanksley et al., 1992 |
| R11 | RAPD | E, EV | Martin et al., 1993 |
| R53 | RAPD | B, D, E, EV, H, X | Martin et al., 1993 |
| R110 | RAPD | B, E | Martin et al., 1991 |
| RS120 | RAPD | E, H | Martin et al., 1991 |
| TG96 | Sheared genomic | E, EV, X | Tanskley et al., 1992 |
| TG100 | Sheared genomic | B, H | Tanksley et al., 1992 |
| TG318 | Pst genomic | none | Tanksley et al., 1992 |
| TG344B | Pst genomic | H | Martin et al., 1993 |
| TG358 | Pst genomic | none | Tanksley et al., 1992 |
| TG379 | Pst genomic | none | Tanksley et al., 1992 |
| TG448 | Pst genomic | none | Tanksley et al., 1992 |
| TG475 | Pst genomic | D, H, | Martin et al., 1993 |
| TG478B | Pst genomic | none | Tanksley et al., 1992 |
| TG503 | Pst genomic | none | Tanksley et al., 1992 |
| TG504 | Pst genomic | B | Martin et al., 1993 |
| TG538 | Pst genomic | B, D, E, EV, H, X | Martin et al., 1993 |
| TG606 | Pst genomic | B, D, E, RV | Martin et al., 1993 |
| TG619 | Pst genomic | E, X | Tanksley et al., 1992 |
| TG638 | Pst genomic | EV | Martin et al., 1993 |
| TM5 | MADS Box gene | B, D, E, H, X | Pnueli et al., 1991*** |

*R. Bernatzky et. al., "Towards a Saturated Linkage Map in Tomato Based on Isozymes a cDNA clones," Genetics, 112:887-98 (1986), which is hereby incorporated by reference.
**S. D. Tanksley et. al., "High Density Molecular Linkage Maps of the Tomato and Potato Genomes," Genetics, 132:1141-60 (1992), which is hereby incorporated by reference.
***Pnueli et. al., "The MADS Box Gene Family in Tomato: Temporal Expression During Floral Development, Conserved Secondary Structures and Homology with Homeotic Genes from Antirrhinum and Arabidopsis," Plant J., 1:255-66 (1991), which is hereby incorporated by reference.
****X = XbaI
E = EcoRI
D = DraI
Ev = EcoRV
B = BstNI
H = HaeIII First, a genome-wide mapping effort placed 1000 RFLP markers on the tomato map and identified 19 markers in the general Pto region which were then surveyed on the Pto near-isogenic lines (NILs) to identify informative clones. Secondly, surveys of the resistant and susceptible NILs were probed with pools of 5 random clones (600 total clones) to identify polymorphic probes. Finally, RAPD analysis using 150 primers of arbitrary sequence (each amplifying about 4 products) was used to identify additional linked markers. The markers identified by the latter two approaches were initially placed on the whole genome map (population 86T64) to confirm their placement to the Pto region. Each marker was then hybridized to survey filters of NILs DNA digested with six restriction enzymes to detect the general level of polymorphism exhibited by the clone and to identify the most easily scored RFLP for mapping purposes. From the 28 markers placed in the Pto region, 18 were found to detect an RFLP between the Pto NILs with at least one enzyme (64%). Most informative markers detected RFLPs with one to three enzymes on these surveys, although two markers—TG538 and R53, detected polymorphisms with all enzymes tested. Subsequently, TG538 was found to detect RFLPs with an additional 7 restriction enzymes. Overall, marker representation was: 3 cDNAs, 4 RAPDs, 10 RFLP markers, and 1 known gene (TM5). The number of informative markers identified from each approach outlined above was: genome-wide mapping (9 markers); multiprobing (4); RAPD analysis (4).

Development and screening of populations segregating for Pto

The majority of the identified markers cosegregated when placed on population 86T64—presumably due to a combination of small population size, lower recombination in this wide cross, and close proximity of the markers. To determine the order of the markers and to estimate linkage distances between them and the Pto gene, we developed a population that was segregating for Pst resistance conferred by Pto.

An $F_2$ population of approximately 1200 plants was developed from a cross between NILs. Since Pto displays dominant gene action, it is necessary to progeny-test any plants resistant to Pst with potential recombination events in the Pto region to determine the allelic state at the Pto locus. In order to avoid progeny testing a large number of plants, we chose to identify and analyze only those plants that were homozygous recessive pto/pto). To accomplish this, we relied on the unusual observation made by French plant breeders that an organophosphorus insecticide, Fenthion, elicits small necrotic lesions on tomato plants carrying the dominant Pto locus (Laterrot, 1985; Laterrot and Moretti, 1989, which are hereby incorporated by reference). It is unknown whether this reaction is a pleiotropic effect of the Pto gene or the result of a tightly linked gene, termed Fen. Whatever the case may be, no plant showing recombination between insensitivity to Fenthion and susceptibility to Pst has been identified in populations of over 650 plants, making this an ideal screen for identifying homozygous susceptible plants.

Approximately 1200 $F_2$ plants were treated with Fenthion, and only those healthy plants (251 total) showing insensitivity (no necrotic lesions) were selected for follow-up. Subsequent work showed that 82% of the plants initially scored as insensitive to Fenthion were susceptible to Pst (pto/pto). Another 16% were heterozygous at Pto and 2% were homozygous resistant (Pto/Pto). A second screen of the 18% misscored plants found that they were in fact sensitive to Fenthion. Thus, pre-screening with the insecticide was not absolutely predictive of the Pto allelic state but did greatly reduce the amount of progeny testing required. A subsequent screening of a segregating population of 419 plants with Fenthion, where the treatment was modified by dipping the plants in a solution of Fenthion instead of spraying them, resulted in a 97% accurate prediction of pto/pto plants (14 misscored plants). Of the 14 misscored plants that were Pst resistant all exhibited Fenthion sensitivity when rescreened.

High resolution linkage analysis

The 251 selected plants were transplanted in the field and analyzed with flanking markers CD31 and TG619 to detect recombinants in the Pto region. A total of 85 such plants were identified and these were then analyzed with the remaining 16 informative markers described above. The 18 markers mapped to 9 loci and spanned a region of almost 20 cM. This is shown in FIG. 1 which is a linkage map of a 20cM region of tomato chromosome 5 developed from the $F_2$ population segregating for Pto. Notably, crossover events identified between many markers that cosegregated in the 86T64 population and the NILs map (population 90GM251) display almost a 10-fold expansion in the Pto region. Over one-half of the map expansion can be accounted for by the distance between TG504 and TG538 (12 cM). In contrast to the TG504–TG538 interval, elsewhere 13 of the markers were found to cluster in a 0.6 cM region. The linkage analysis also revealed that one marker, TG538, cosegregated with the Pto locus.

Considering the size of the population and the corresponding standard error, TG538 lies less than 0.6 cM (95% confidence interval) from Pto. This discovery of tight linkage to Pto is especially interesting in light of the fact that TG538 is clearly derived from a region highly divergent between *L.esculentum* and *L.pimpinellifolium*, as evidenced by the high level of polymorphism detected by this marker (See FIG. 1).

Determination of physical distance in the Pto region

Because our goal is to use the linkage map to isolate the Pto gene, we used pulsed field gel electrophoresis (PFGE) to estimate the maximum physical distance encompassed by the intervals on each side of TG538. A total of 8 rare-cutting restriction enzymes were surveyed (BssHII, NarI NruI, MluI, SacII, SfiI and SmaI). Those five enzymes which gave fragments between 100 and 900 kb when probed with TG538 were followed up by probing with TG475 and TG504.

The experiments revealed that TG538 and TG475 detected 19 identical restriction fragments ranging in size from 340 kb to more than 800 kb. In only two enzyme digests, MluI and SfiI, were unique fragments identified to differentiate these two markers. In all cases, the two NILs were distinguished by RFLPs using PFGE. For TG475, the degree of polymorphism was even higher than when six-base-pair recognition enzymes were used. Although the smallest fragment hybridizing to both TG538 and TG475 was 340 kb (with NruI), this fragment only occurred in the Pst susceptible line, Rio Grande. Since insertions or deletions could exist in this region that differ between the resistant and susceptible lines, we were primarily interested in the smallest common fragment that existed in Rio Grande-PtoR. The analysis showed that two fragments of 435 and 450 kb were in common between TG475 and TG538 (SalI and SfiI digests) in Rio Grande-PtoR. Thus, TG475 and TG538 are located no further apart than this distance on the chromosome. The minimum distance between them cannot be determined from these data. A distance of only 400–500 kilobases indicated that we would be able to use chromosome walking (map-based cloning) to isolate the Pto gene.

B. Using TG538 to isolate a YAC clone spanning Pto region

Figure 2:
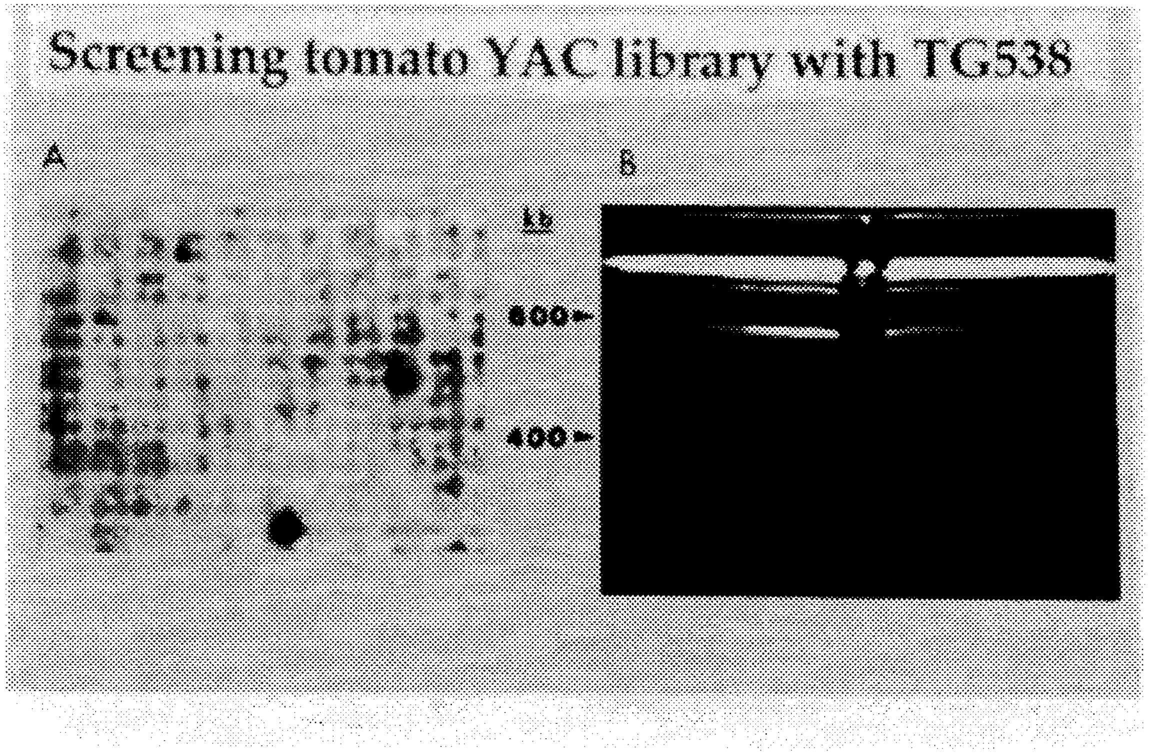
FIG. 2A shows an example of screening the YAC library with DNA markers.
FIG. 2B shows a gel separation of a YAC clone using pulsed field gels. PTY538-1 is at 400 kb. Another YAC (not relevant) was analyzed at 600 kb.
Figure 3:
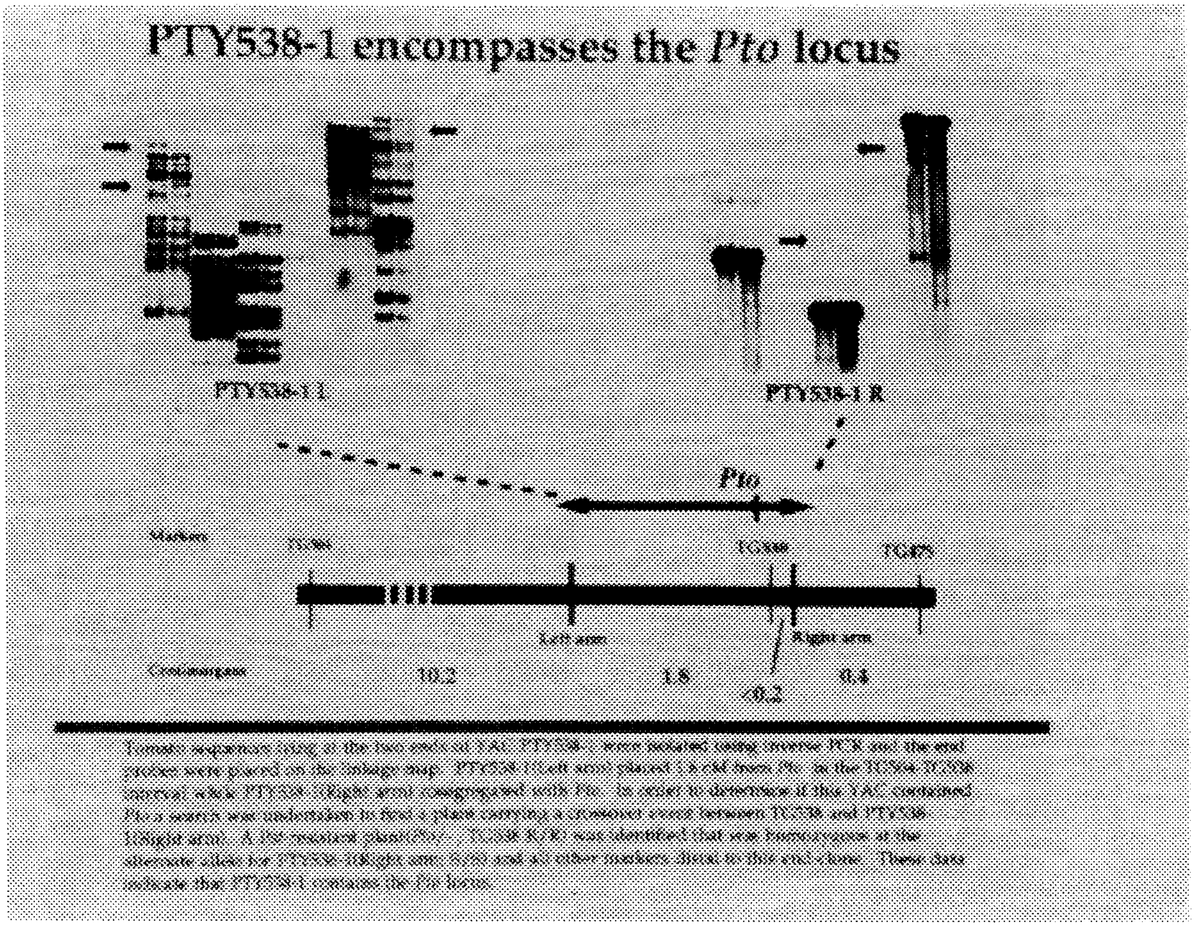
FIG. 3 shows genetic mapping of two end clones from PTY538-1.

RFLP marker TG538 was used to screen a tomato YAC library and a 400 kilobase (kb) clone, PTY538-1, was identified as hybridizing to this marker. End-specific probes corresponding to the right (PTY538-1R) and left (PTY538-1L) arms of PTY538-1 were isolated by inverse PCR and placed on the high resolution linkage map of the region. PTY538-1L mapped 1.8 centimorgans from Pto, while PTY538-1R cosegregated with Pto. In order to confirm that PTY538-1R encompassed Pto, it was necessary to identify a plant with a recombination event between PTY538-1R and Pto. We therefore used markers TG538 and PTY538-1R to analyze a total of 1300 plants from various $F_2$ populations, $F_3$ families, and over 50 cultivars. One plant was homozygous for the PTY538-1R allele associated with pto (susceptible allele). All progeny from this plant were resistant to Pst, indicating that the plant was homozygous Pto/Pto. This result indicated that PTY538-1 spanned the Pto locus. FIG. 2A shows an example of screening the YAC library with DNA markers. FIG. 2B shows a gel separation of a YAC using pulsed field gels. PTY538-1 is at 400 kb. Another YAC (not relevant) was analyzed at 600kb. FIG. 3 shows genetic mapping of two end clones from PTY538-1.

C. Screening a leaf tissue cDNA library with PTY538-1.

DNA from PTY538-1 was isolated from agarose after separation on a clamped homogeneous electric field (CHEF) gel, and used to probe approximately 920,000 plaque-forming units of a leaf cDNA library.

The cDNA library was constructed by inoculating (i.e. dipping) six-week-old plants of Rio Grande-PtoR and TA208 (Pto/Pto) into a solution of arivulent Pst strain PT11 ($4 \times 10^7$ colony-forming-units/ml), 10 mM $MgCl_2$, and 0.05% L-77 Silwet (Union Carbide, Southbury, Conn.) dispersed in distilled water. Leaf tissue was harvested at 2,6,22,48, and 72 hours after inoculation, polyA$^+$ RNA was prepared from each sample, and equal amounts were pooled before library construction The cDNA library was constructed in vector λgt10 using a mixture of random and oligo(dT) primers (Stratagene, La Jolla, Calif.).

Figure 4:
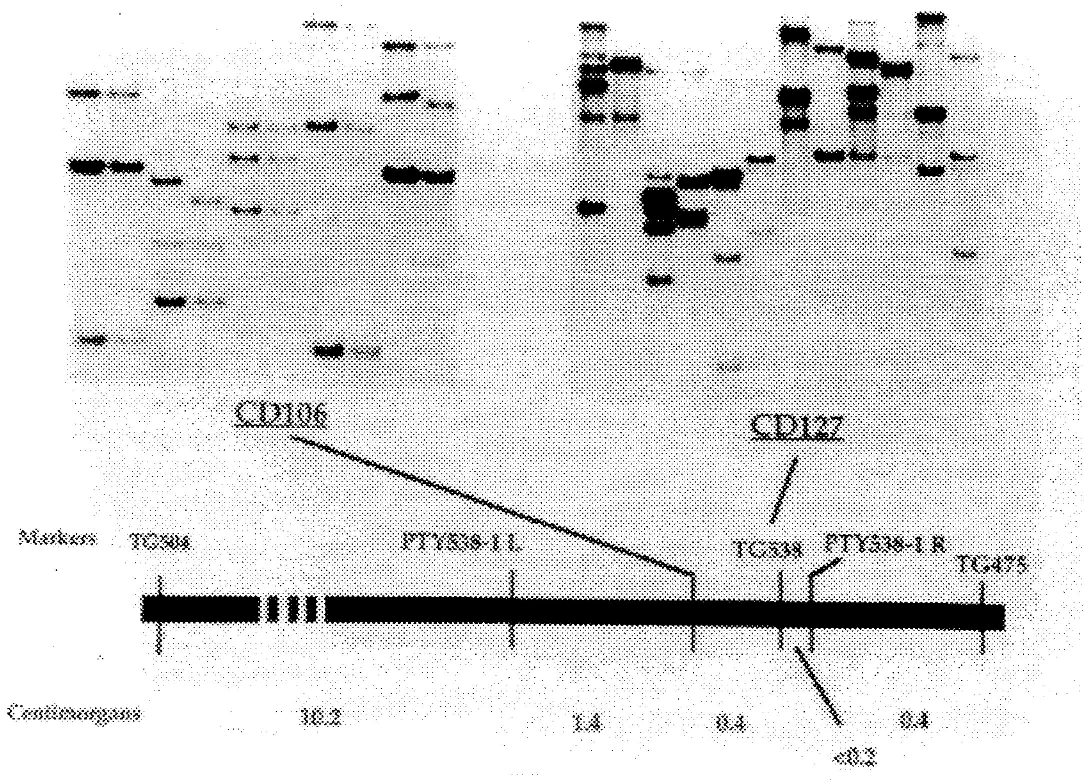
FIG. 4 shows genetic mapping of cDNA clones CD106 and CD127.

From approximately 200 hybridizing plaques, 30 were investigated further. The cDNA inserts were amplified by PCR and used to probe a tomato mapping population consisting of 85 plants with recombination events in the Pto region. Two of the clones, CD127 and CD146 (both 1.2 kb), contained sequences that cross-hybridized. When CD127 was mapped, it cosegregated with Pto, as shown in FIG. 4. The genetic cosegregation of CD127 with Pto and the fact that the cDNA was isolated from a leaf tissue library made this cDNA a strong candidate for the Pto gene.

CD127 hybridized to numerous polymorphic fragments when probed on blots of genomic DNA from Rio Grande-PtoR and Rio Grande plants. This indicated that the clone might contain exons spanning a large region or that it represented a family of related genes. To distinguish between these possibilities, we probed the leaf cDNA library with the CD127 insert and isolated an additional 14 cross-hybridizing clones, ranging from 0.6 to 2.4 kb. The cDNA clone CD186 was isolated from this rescreening of the cDNA library.

Figure 5:
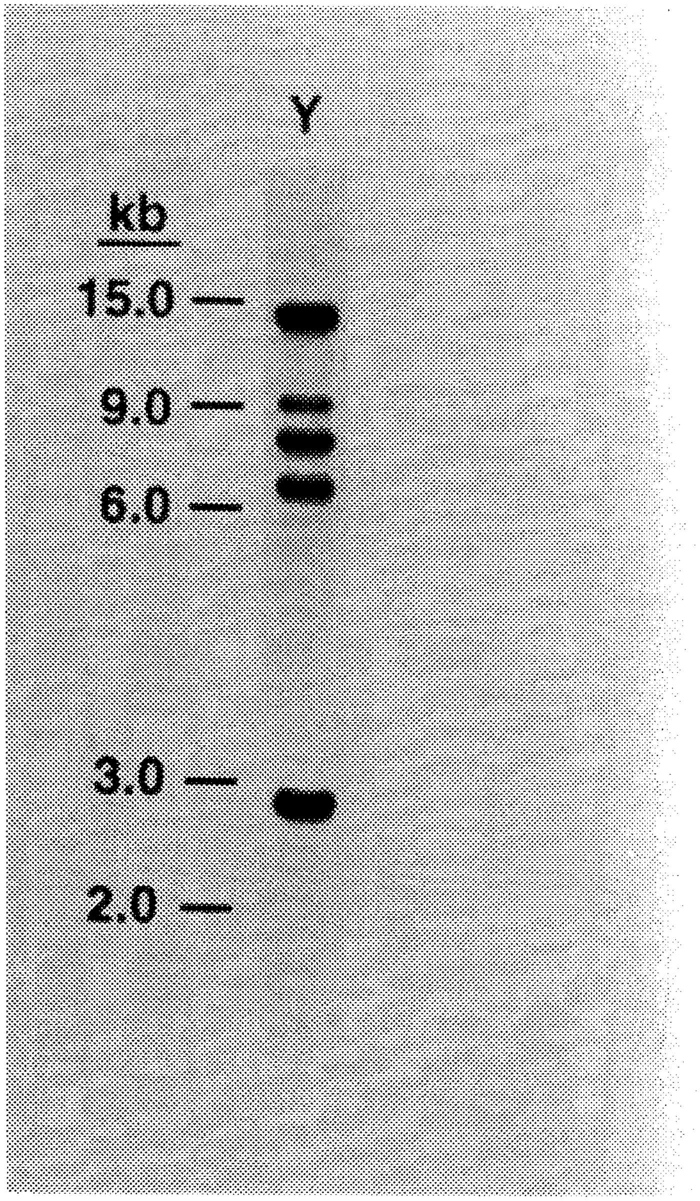
FIG. 5 is a DNA blot analysis of YAC PTY538-1 (lane Y). Total yeast DNA from PTY538-1 was digested with BstNI, separated on a 1% agarose gel and blotted onto Hybond N+ membrane. The membrane was probed with $^{32}P$-labeled CD127 insert.

Oligonucleotide primers were designed using partial sequence data from both ends of CD127, and used in PCR to amplify a product from the insert of the cDNA clones. PCR products were digested with restriction enzymes recognizing 4-base pair sites (e.g., HaeIII, HinfI, TaqI), and the fragments were separated in a gel composed of 3% Nusieve GTG agarose (FMC) and 1% ultrapure agarose. Six different cDNA types were identified in Rio Grande-PtoR based on their pattern of restriction fragments with homology to CD127. To investigate the genome location of the family members, total DNA from the YAC transformant PTY538-1 was digested with BstNI and analyzed by DNA blot hybridization. The YAC contained all of the CD127-hybridizing fragments, with the exception of a 5 kb band that is common to both Rio Grande-PtoR and Rio Grande. CD127, therefore, represents a gene family that is clustered primarily at the Pto locus. This is shown in FIG. 5.

Example 2

Determination of the DNA sequence of CD127 and CD186.

A. Transfer of cDNA inserts to vectors for DNA seguencing.

Figure 6:
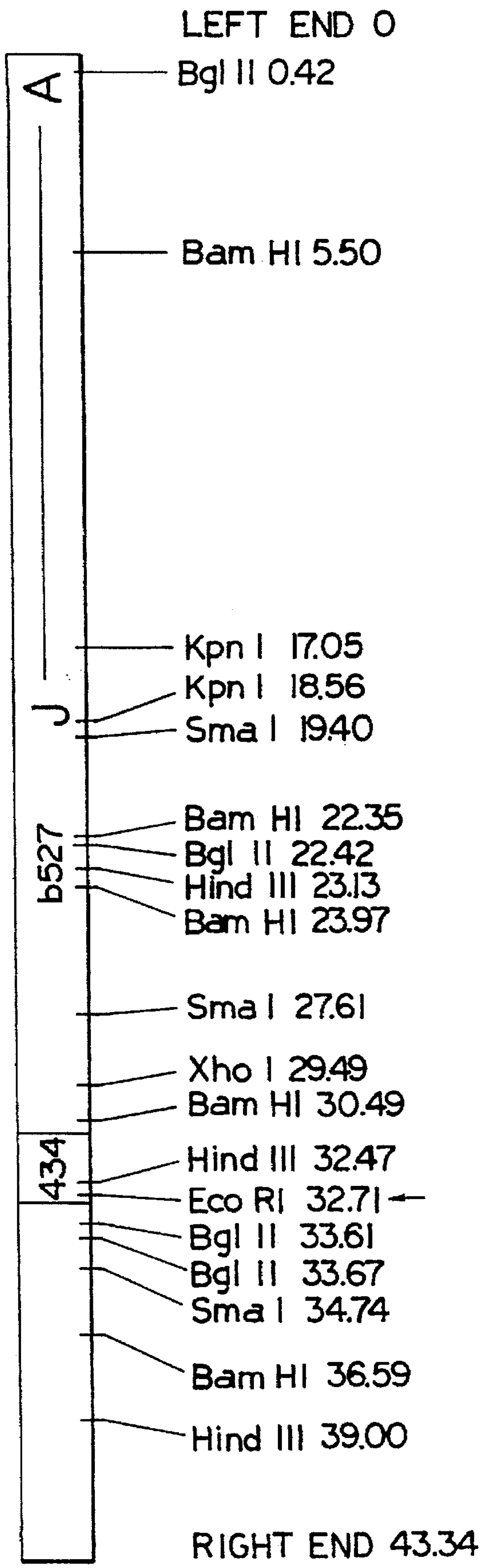
FIG. 6 is a map of cloning vector lambda gt10.
Figure 7:
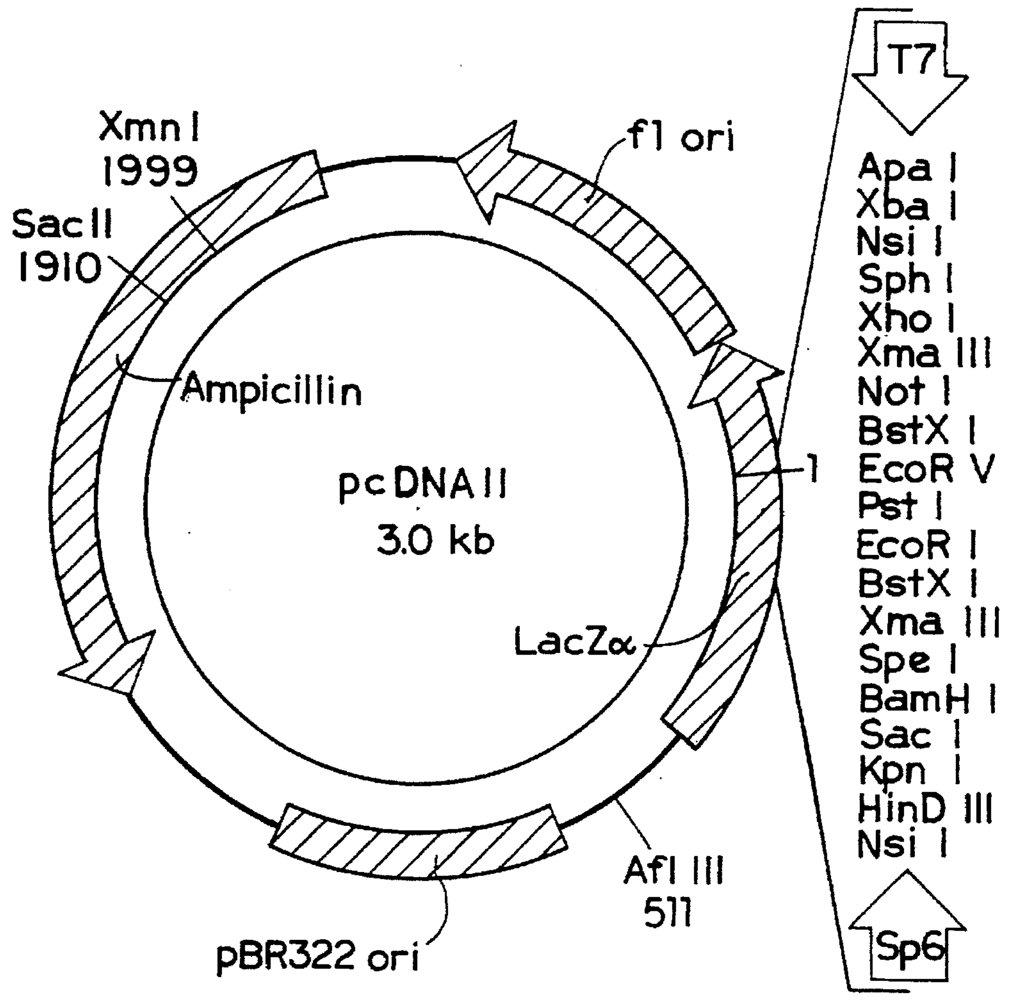
FIG. 7 is a map of plasmid vector pcDNAII. pcDNAII has a length of 3013 nucleotides, a first nucleotide of +1, a polylinker at bases 10–122, an Sp6 promoter at bases 136–152, ampicillin resistance at bases 1331–2191, F1 origin at bases 2377–2832, Lac Z gene at bases 2832–390, and a T7 promoter at bases 2993–3012.
Figure 8:
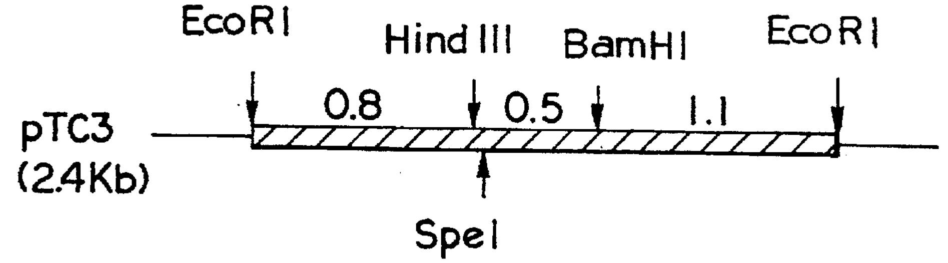
FIG. 8 is a map of plasmid vector PTC3.

CD127 and CD186 were originally isolated as cDNA clones in the cloning vector lambda gt10 (see FIG. 6). Because this vector is difficult to manipulate we re-cloned the inserts from CD127 and CD186 into a new vector pcDNAII (see FIG. 7), from Invitrogen, Corp., San Diego, Calif. The inserts were removed from lambda gt10 as EcoRI fragments and cloned into the EcoRI site of pcDNAII, creating two new plasmids: PTC1 (CD127 in pcDNAII) and PTC3 (CD186 in pcDNAII). See FIG. 8 which is a map of plasmid vector PTC3. These plasmids were used for sequencing the cDNA inserts using standard dideoxy double stranded sequencing techniques (Sequenase Kit, United States Biochemical Corp., Cleveland, Ohio) and oligonucleotide primers designed to prime at approximately 200 base pair intervals throughout the sequence. Some DNA sequence was also determined at the Purdue University Center for AIDS Research using an automated DuPont Genesis 2000 Instrument. The entire sequence was determined on both strands. The resulting sequence data was analyzed using the program MacVector and overlapping fragments were aligned to create one contig spanning the entire insert.

B. Determination of Sequences.

The entire 2443 base pair DNA sequence of the CD186 insert (SEQ. ID. No. 3) was determined to be as follows:

| | | | | | | |
|---|---|---|---|---|---|---|
| 1 | GAATTCGGCA | CGAGCTTAAA | TAATGTTATT | TGAAGGTTAT | TAAGTTGTAC | TCAAGTCTCA |
| 61 | ATCATGGGAA | GCAAGTATTC | TAAGGCAACA | AATTCCATAA | ATGATGCTTT | AAGCTCGAGT |
| 121 | TATCTCGTTC | CTTTTGAAAG | TTATCGAGTT | CCTTTAGTAG | ATTTGGAGGA | AGCAACTAAT |
| 181 | AATTTTGATC | ACAAGTTTTT | AATTGGACAT | GGTGTCTTTG | GGAAGGTTTA | CAAGGGTGTT |
| 241 | TTGCGTGATG | GAGCAAAGGT | GGCCCTGAAA | AGGCGTACAC | CTGAGTCCTC | ACAAGGTATT |
| 301 | GAAGAGTTCG | AAACAGAAAT | TGAGACTCTC | TCATTTTGCA | GACATCCGCA | TCTGGTTTCA |
| 361 | TTGATAGGAT | TCTGTGATGA | AAGAAATGAG | ATGATTCTAA | TTTATAAATA | CATGGAGAAT |
| 421 | GGGAACCTCA | AGAGACATTT | GTATGGATCA | GATCTACCCA | CAATGAGCAT | GAGCTGGGAG |
| 481 | CAGAGGCTGG | AGATATGCAT | AGGGGCAGCC | AGAGGTCTAC | ACTACCTTCA | TACTAGAGCA |
| 541 | ATTATACATC | GTGATGTCAA | GTCTATAAAC | ATATTGCTTG | ATGAGAATTT | TGTGCCAAAA |
| 601 | ATTACTGATT | TTGGAATATC | CAAGAAAGGG | ACTGAGCTTG | ATCAAACCCA | TCTTAGCACA |
| 661 | GTAGTGAAAG | GAACTCTCGG | CTACATTGAC | CCTGAATATT | TTATAAAGGG | ACGACTCACT |
| 721 | GAAAAATCTG | ATGTTTATTC | TTTCGGTGTT | GTTTTATTCG | AAGTTCTTTG | TGCTAGGTCT |
| 781 | GCCATAGTTC | AATCTCTTCC | AAGGGAGATG | GTTAATTTAG | CTGAATGGGC | AGTGGAGTCG |
| 841 | CATAATAATG | GACAGTTGGA | ACAAATCGTA | GATCCCAATC | TTGCAGATAA | AATAAGACCA |
| 901 | GAGTCCCTCA | GGAAGTTTGG | AGATACAGCG | GTAAAATGCT | TAGCTTTGTC | TAGTGAAGAT |
| 961 | AGGCCATCAA | TGGGTGATGT | GTTGTGGAAA | CTGGAGTATG | CACTTCGTCT | CCAAGAGTCT |
| 1021 | GTTATTTAAG | ATATTTTTGT | TTTTCTGAGT | TTTATATAGA | AAAAGGTAAA | CTTTGAAAAC |
| 1081 | TTGAATTGCT | ATACCTGTGG | ATCCTTCTTT | CATTTTATTA | GGTGCGTCCG | GCTGTTACAC |
| 1141 | ATATTGTATA | TGGTTCTTAT | TAAGTTCTTC | AGACATTTTG | TTATTGTAAA | GAGGCAAAAA |
| 1201 | GGAAGTTTGC | TGCTTTGACA | TAGTCAATCT | AAAACTATAT | ACATTCAACT | TTCAGAATGG |
| 1261 | AACTATAAAA | GTTTGTGGAG | CAATTCAAAA | TGTTACTCAA | CCTGTTCACA | AAATGACTAT |
| 1321 | TGTAGAGCAA | TAATGGTTAT | AATATATAAC | CATTATTGAG | TAATATTTTT | GTAGTAGTAT |
| 1381 | TGCCCAAGTC | CATTAGCGGA | GAGGTAATTT | TCTTTTTGGT | TCTCTCTTCC | ACAATAGCTA |
| 1441 | TCAATCTCTC | TGTCTTCTCG | CTAAATTTCC | TCAGTTGTGG | TATAATCAGA | GGTTCCTAAG |
| 1501 | CCTTCTGTTT | TGTATACATA | TATTTGTGAT | TTTCATCTAT | CATGCTTACT | GTTAGGAGTT |
| 1561 | ATATTGCTTG | ATGAGAATTT | TGTGGCAAAA | ATTAATGATT | TTGGTCGATT | CAAGAAGCTT |
| 1621 | GATCAAACCC | ATGTTACCAC | AATAGTAAAG | GAACTTTTGG | TTACCTTGAC | CCTGAATATT |
| 1681 | ATCAAACTAG | TCAGCTGACA | GAAAAATCTG | ATGTTTATTC | TTTCGGTGTT | GTTTTATTAG |
| 1741 | AAGTTATTTG | TGCTAGGCCT | GCGCTGGATT | CATCTCGTTC | GAGGGAGATG | GTCAGCTCAG |
| 1801 | TTAAATGGGC | AAAGGAGTGT | CAGAAGAACG | GACAGTCGGA | ACGAATTATA | GATCCCAATC |
| 1861 | TTGTTGGCAA | AATAAGACCA | GATTCCCCCA | GGAAGTTTGG | AGAAACAGCT | GTGAAATGCT |
| 1921 | TAGCTGAAAC | TGGCGTAAAC | AGGCCATCAA | TGGGTGAGGT | GCTCGAGAAA | CTGGACTATG |
| 1981 | CACTTCATCT | CTAAGAGCCT | GTCATTCAAG | AAAACAGTAC | CATCCCTATC | CGCGAGCAAA |
| 2041 | TCAATGATTT | CAGTCATGTT | GATGACACTT | CCTCTGCTTC | TTCGGTCAAA | ATTGGGCTGA |
| 2101 | TCTCTAGTAT | GAATGCGTTC | AGATTTTGCT | CAAGAAAACA | GCCGGGAGAA | GTTCAATTAA |
| 2161 | TGGTTGCACT | CCATGGGAAC | CAACTATTCC | AAGCCAACAA | CTTCCATAAA | TGATGCTTCC |
| 2221 | AATTTGAGTA | ATCGCGTTCC | TTTTGAAAGT | TTTCGAGTTC | CTTTTGTAGA | TTTGCAGGAA |
| 2281 | GCAACTAATA | ACTTTGATGA | CAAGTTTCTG | ATTGGAGTGG | GTATATTTGG | TAAGGATTAC |
| 2341 | AGGGGTGTTT | TGCGTGATGG | TACAAAGGTG | GCCCTGAAAA | GACATAAGCC | TGAGTCTCCA |
| 2401 | CAAGGTATTG | AAGAGTTCCG | AACAGAAATC | TCGTACCGAA | TTC | |

A 963 bp open reading frame sequence (ORF1) (SEQ. ID. Nos. 1 and 2) was found in the region nearest to the 35S CaMV promoter in pPTC8 (see FIG. 9). ORF1, hereafter referred to as Pto, encodes a 321 amino acid hydrophilic protein. ORF1 and the corresponding amino acid sequence were identified using the program MacVector.

Example 3

Incorporation of CD127 and CD186 inserts into plant expression vectors.

A. Cloning of CD127 and CD186 inserts into expression vector pBI121.

The cloning of CD127 and CD186 inserts into expression vectors began with the plasmids PTC1 and PTC3. To prepare the inserts of PTC1 and PTC3 for transformation into plants, the inserts were first cloned into the Ti-based plant transformation vector pBI121 (see FIG. 10) from Clontech Laboratories, Palo Alto, Calif. Two cDNA clones, representative of the two size classes of transcripts, were subcloned into pBI121: (CD127 [1.2 kb] and CD186 [2.4 kb]). Based on the DNA sequence information, the sense orientation 5 of each fragment was determined and the cDNA inserts were placed in the sense orientations in pBI121 under the transcriptional control of the constitutive cauliflower mosaic virus (CaMV) 35S promoter. The resulting plasmids were designated pPTC5 (CD127, [PTC1 insert]) and pPTC8 (CD186, [PTC3 insert]) (see FIG. 9). The constructs were introduced into *Agrobacterium tumefaciens* LBA4404 by electroporation. The bacteria containing pPTC5 and pPTC8 were used to transform cotyledon explants of Pst-susceptible tomato cultivar, Moneymaker.

Example 4

Method for Transforming Tomato

Sterile cotyledon explants of Example 3 from approximately week old seedlings were incubated for 10 minutes in an *Agrobacterium tumefaciens* (LBA4404) harboring either the CD186 or CD127 T-DNA plasmid. Explants were then transferred to TRS medium (containing 70 mg/l kanamycin as a selective agent for plant cells harboring the T-DNA insertion) with media changes as needed at approximately 1 month periods or until shoots had formed.

The TRS medium was prepared by blending 500 ml of water with 100 ml MS major salts, 10 ml MS minor salts, 5 ml MS iron stock, 1 ml B5 vitamin stock, and 30 g sucrose. The pH was measured to ensure that it was at 5.8. 500 ml of the mixture was blended with 4.0 g agar, autoclaved, and cooled to 45° C. To the cooled mixture, 0.5 ml zeatin (1 mg/ml), 0.05 ml IAA (1 mg/ml), 1 ml kanamycin (25 mg/ml), and 1 ml timentin (200 mg/ml) or 1.25 ml carbenicillin (200 mg/ml) were added.

5 mm shoots were excised and placed on P rooting medium. P rooting medium was prepared by blending 100 ml P major salts, 1 ml P minor salts, 5 ml MS iron stock, 2.5 ml MS thiamine stock, 10 ml MS myolnositol stock, 1 ml nicotinic acid (0.5 mg/ml), 1 ml pyridoxine (0.5 mg/ml), 1 ml glycine (2 mg/ml), and 30 g sucrose and the volume of that mixture was adjusted with distilled water to 500 ml. The pH of the mixture was then measured to ensure that it had a pH of 5.8, and 4.0 g Agar was added to 500 ml of the mixture. The mixture was then autoclaved and cooled to 45° C. 0.09 ml IAA (1 mg/ml), 1.0 ml kanamycin (25 mg/ml), and 1 ml timentin (200 mg/ml) were added to the mixture.

Healthy green plants with good root formation were then removed from magenta boxes, transferred to a soil mix, moved to a greenhouse, and screened with *Pseudomonas syringae*.

Putative transformed plants were verified through analysis of genomic plant DNA using both a PCR assay for presence of the CaMV 35S promoter (forward primer= AAAGGAAGGTGGCTCCTACAAAT (SEQ ID. No. 4), reverse primer=CCTCTCCAAATGAAATGAACTTCC (SEQ ID. No. 5)) and via Southern probing using the CaMV35S promoter sequence and CD127 insert DNA as probes. Only plants confirmed to be transformed by one or both of these assays were utilized for further experiments.

Example 5

Determination of Pst resistance in transformed plants.

A. Initial testing for Pst resistance in transformed plants.

Five weeks after the transformed plants were transferred to soil, single leaves were inoculated with Pst strain Ti(pPTE6) carrying avrPto. Leaflets were inoculated by dipping into a solution of avirulent Pst strain T1 (pPTE6) ($2\times10^7$ colony-forming-units/ml), 10 mM $MgCl_2$, and 0.05% L-77 Silwet (Union Carbide, Southbury, Conn.) dispersed in distilled water. Under these conditions, symptoms of bacterial speck appeared after 5–7 days on susceptible plants. A resistant reaction was indicated by the absence of necrotic specks on the inoculated leaves. A susceptible reaction was indicated by numerous necrotic specks surrounded by chlorotic halos. Reactions were scored 8–10 days after inoculation. As controls, 4 week-old seedlings of Rio Grande-PtoR, Moneymaker, and Moneymaker transformed with pBI121 alone were also inoculated. Of two plants that were confirmed to contain the integrated transgene from pPTC8 (PTC8/39 and PTC8/56) both were resistant to Pst strain T1(pPTE6). None of the nine transformants containing integrated copies of pPTC5 displayed resistant phenotypes.

B. Genetic analysis to confirm that Pst resistance is conferred by CD186 transgene.

Figure 10:
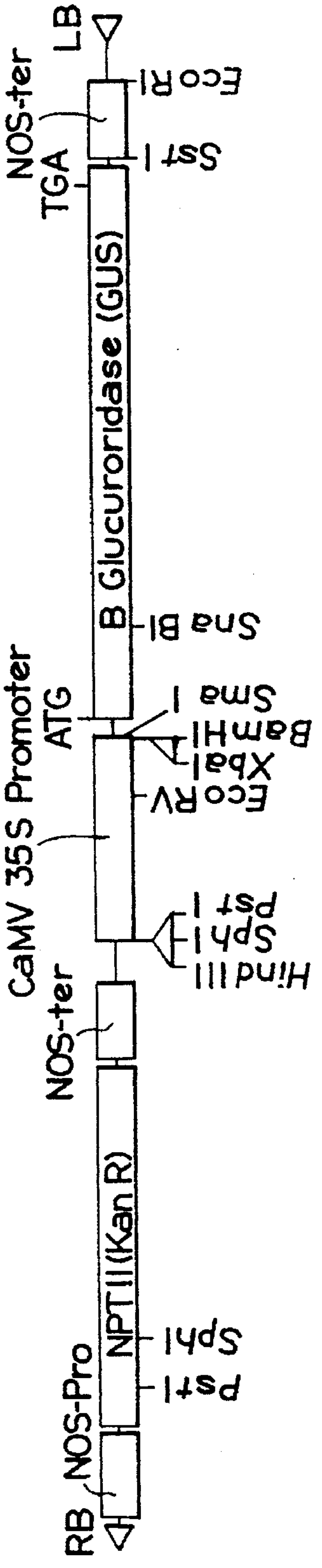
FIG. 10 is a map of the T-DNA region of plasmid vector pBI121.
Figure 11:
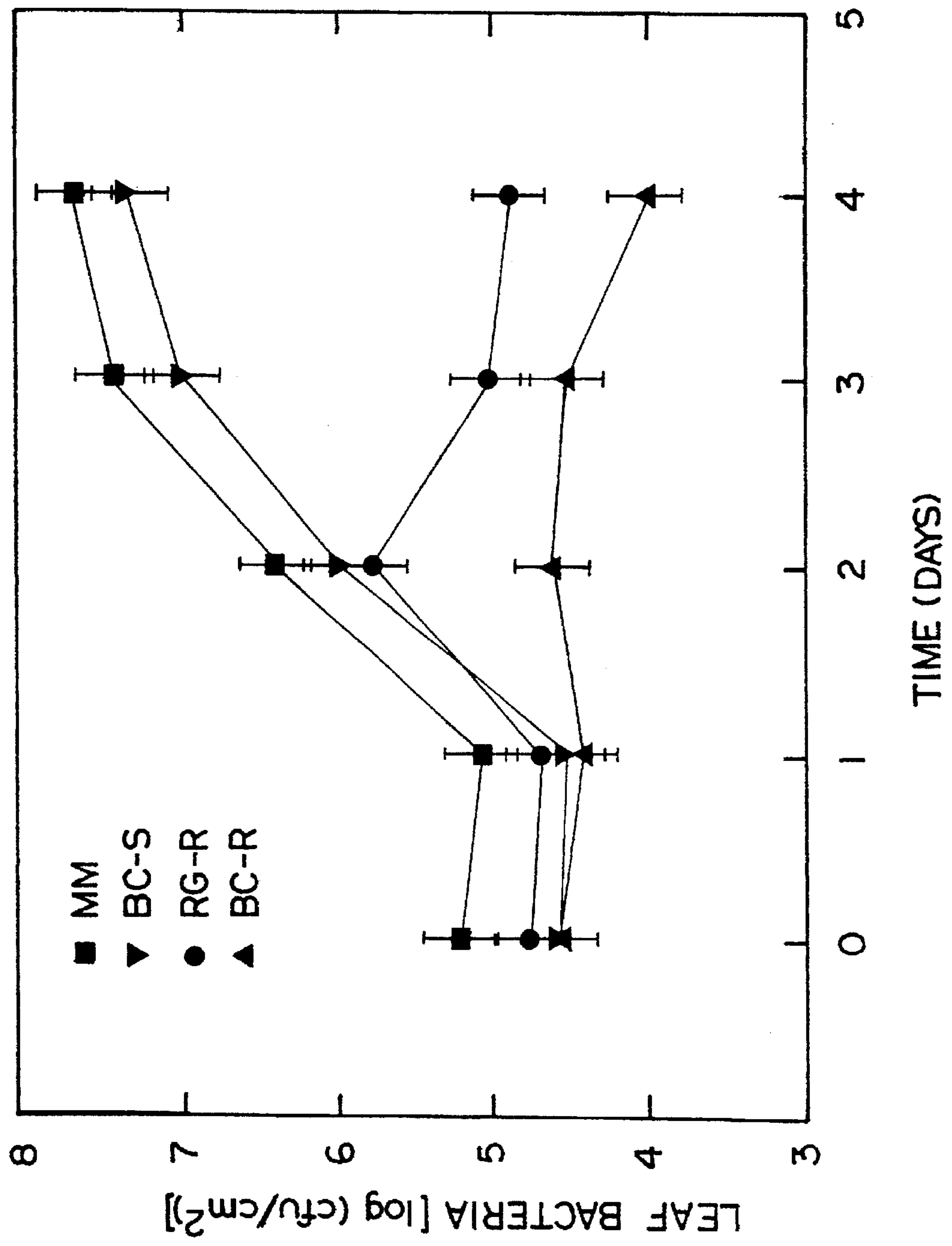
FIG. 11 is a plot of leaf bacteria versus time with the plotted value being means of 3 samples, each consisting of 3 leaf disks and error bars indicating standard deviations.

To confirm that Pst resistance was due to introduction of the CD186 cDNA insert, a resistant RO transgenic plant (PTC8/39) was crossed to a susceptible control plant (cv. Rio Grande). Of 22 backcross progeny examined, 9 inherited the CD186 transgene. This closely fit a 1:1 segregation ratio and indicated that the original integration of pPTC8 sequences in PTC8/39 occurred at a single locus. The same 9 plants containing the CD186 transgene displayed no disease symptoms upon inoculation with Ti(pPTE6). This indicates that CD186 transgene was sufficient for conferring resistance in a normally Pst-susceptible tomato cultivar. The remaining 13 plants lacked the CD186 transgene and displayed typical symptoms of bacterial speck. All 22 progeny plants were susceptible to Pst strain T1 which lacks avrPto. Because it is possible that plants showing no disease symptoms in response to Ti(pPTE6) might still harbor a large population of Pst, we monitored the colony-forming-units of Pst in the progeny plants and in control over plants over a period of 4 days after inoculation and plotted the number of leaf bacteria versus time (see FIG. 11). FIG. 10 shows the growth of Pst in the leaves of 7-week-old Rio Grande-PtoR ("RG-R"), Moneymaker ("MM"), backcross progeny with pPTC8 ("BC-R"), and without pPTC8 ("BC-S") lines of tomato which were inoculated with Pst strain T1 (pPtE6) and then had bacterial populations determined at specified points in time. The plotted values were means of 3 examples, each consisting of 3 leaf disks. Error bars indicate standard deviations. The 9 progeny (BC-R) exhibiting no disease symptoms contained $10^3$-fold fewer bacteria per $cm^2$ leaf area than the BC-S susceptible plants at the end of this time period. Lower bacterial populations in BC-R plants than in Rio Grande-PtoR plants were observed and may be the result of a higher abundance of Pto protein in BC-R plants due to the constitutive 35S promoter. Thus, CD186 functionally complements Pto in Pst-susceptible plants by inhibiting growth of the Pst population and suppressing symptoms of bacterial speck disease.

Example 6

Determining if DNA sequences in other crop species have homology to Pto.

A. Southern blot analysis of genomic DNA from a variety of crop species using as a probe CD127 and CD186 insert DNA.

Figure 12:
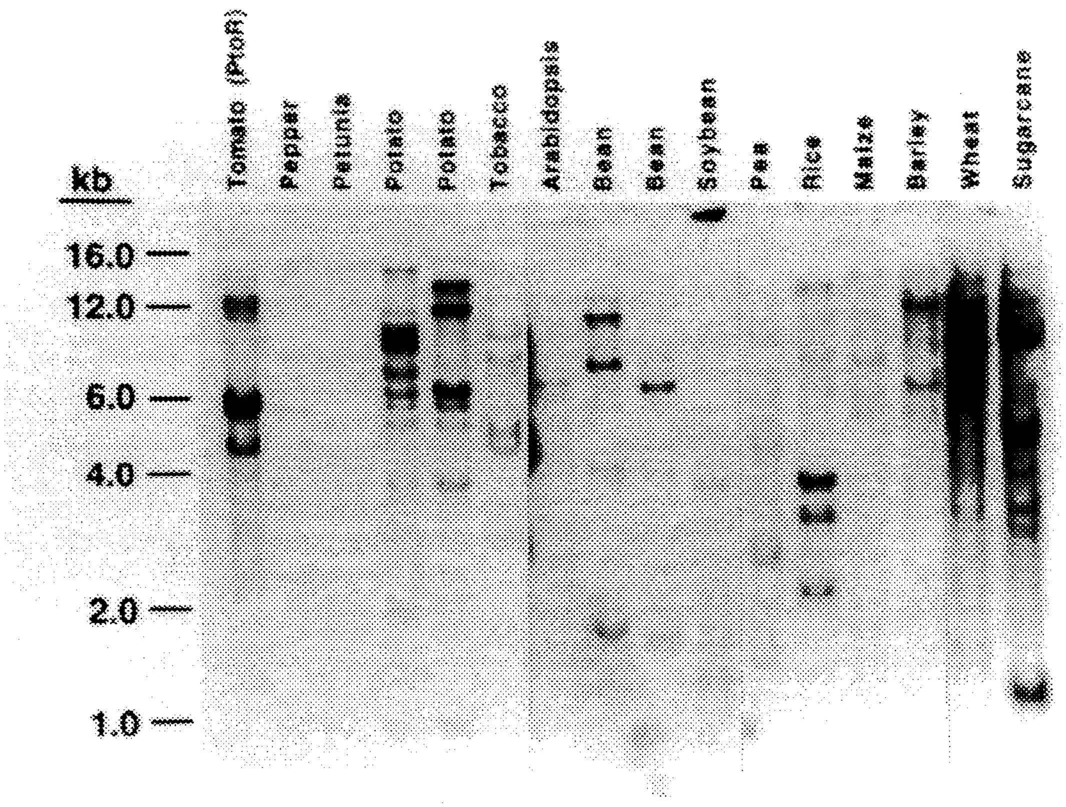
FIG. 12 shows a DNA blot analysis of plant species distribution of Pto gene homologs.

To determine if homologs of the CD127 gene family were present in other plant species, we performed Southern blot analysis on genomic DNA isolated from the following plants and digested with EcoR1 (amount loaded on gel is indicated): tomato (Rio Grande-PtoR, 3 ug); pepper (*Capsicum annum*, 5 ug); petunia (*Petunia parodii*, 5 ug); tobacco (Samsun, 5 ug); Arabidopsis (Col-0, 1 ug); bean (*Phaseolus acutifolius*, G40178, 3 ug); bean (*P. acutifolius*, PO310800, 3 ug); soybean (Centennial, 4 ug); pea (Sparkle, 10 ug); rice (IRAT, 3 ug); maize (RI 24, 15 ug); barley (SE16, 15 us); wheat (R-4, 15 ug); sugarcane (*Saccharum spontaneum*, SES208, 10 ug). The digested genomic DNA was separated by electrophoresis on a 1% agarose gel. The gel was blotted onto Hybond N+ membrane which was hybridized with radiolabeled CD127 insert using random-hexamer $^{32}P$-labeled (a.p. Feinberg, B. Bogelstein, *Anal. Biochem.* 132, 6 [1938]) PCR product (1–2×10$^6$ cpm/ml buffer) amplified from the cDNA clone. Filter was washed to 0.5×SSC at 65° C. and exposed to film for 24 hours for the Solanaceous species (lanes 1–6) and 7 days for the remaining species (lanes 7–16). FIG. 12 shows the resulting DNA blot analysis of the species distribution of Pto gene homologs. Homologs of CD127 were identified in all species examined. Multiple bands were detected in many of the species, indicating the possible presence of a gene family similar to that in tomato. This sequence conservation indicates that other plant species appear to contain genes with structural, and perhaps functional, similarity to the CD127 gene family. Consistent with this, some soybean cultivars exhibit hypersensitive resistance in response to avrPto.

Similar experimentation using CD186 as a probe yielded results substantially identical to that achieved with CD127.

Example 7

Homology of CD186 with Other Known Genes

FIG. 13A is a physical map of the CD186 cDNA insert for ORF1 (Pto) and the 35 S CaMV promotor on pPTC8 with the regions designated a' and b' being homologous to a and b on ORF1 and maybe representing a downstream pseudogene. The numbers above the map are DNA base pairs, with the numbers in parentheses referring to positions in ORF1 corresponding to a' and b'. FIG. 13B is the deduced amino acid sequence of ORF1 (Pto) shown in standard 1-letter code.

The deduced amino acid sequences from the open reading frames of CD186 and CD127 were run against Genebank release 77 using the BLAST program (Altschul, et al. *J. Mol Biol* 215:403 (1990)). Highly significant matches were found with a variety of protein kinases from plants and animals. Eleven subdomains, including 15 invariant amino acids, characteristics of protein kinases, were also found to be present in both the CD186 and CD127 amino acid sequences. Furthermore, sequences indicative of serine/threonine kinases occur in subdomains VI (consensus DLKPEN) and VIII (consensus (G(T/S)XX(Y/F)XAPE). This is shown in FIG. 13B where the positions of these subdomains characteristic of protein kinases are indicated in parenthesis above the sequence, while the amino acids that are highly conserved among protein kinases are underlined. Residues that indicate serine/threonine specificity are double-underlined. A site at the N-terminus is overlined which may be modified by the addition of myristic acid (a potential myristoylation site).

To examine further the relationship to protein kinases, the CD186 amino acid sequence was compared to the Protein Kinase Catalytic Domain Database (Hanks and Quinn *Meth Enzymol* 200:38 (1991)) using the align function of MacVector sequence analysis software (Kodak international Biotechnologies, version 4.0.1). The five most similar matches were to putative serine/threonine protein kinase genes of plant origin (L00670, M84659, ZMPK1), including three with unknown roles from Arabidopsis (TMK1, GenBank accession number L00670; ARK1, M80238; RLPK, M84659) one with an unknown role from maize (ZMPK1, X5238), and one from Brassica (SRK6, M76647) that is believed to be involved in pollen/stigma recognition and, like tomato-Pst to be based on a gene for gene interaction (pollen/cell/stigma) (SRK6, M76647) (Stein et al. *Proc Natl Acad Sci USA* 88:8816 (1991). The similarity between Pto and SRK6 is particularly interesting since SRK6 appears to be involved in a specific cell-cell interaction (pollen cell/stigma papillar cell) that, like tomato-Pst, is based on a gene-for-gene relationship. Other than plants, the closest matches in the data base were to mammalian serine/threonine kinases of the Raf family (Bonner et al. *Nucl Acids Res* 14:1009 (1986) and (MacIntyre et al. *Mol Cell Biol* 7:2135 (1987).

Example 8

Examination of differences in transcript size or abundance between tomato lines for resistance Pst.

A. Analysis by Northern blots of transcript size and abundance.

Figure 14:
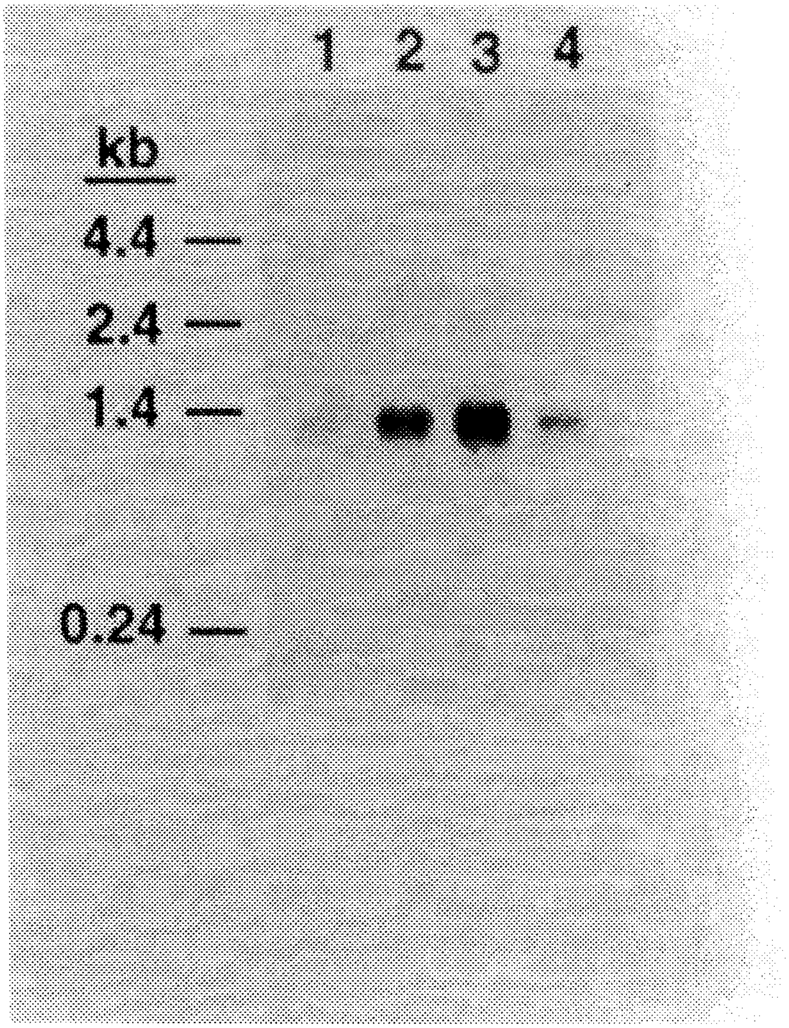
FIG. 14 is an RNA blot analysis of Pto gene family transcripts. PolyA+RNA of Rio Grande (pto/pto; lane 1), Rio Grande-PtoR (Pto/Pto; lane 2), Spectrum 151 (pto/pto; lane 3) and Moneymaker (pto/pto; lane 4) was isolated from leaf tissue of 5 week-old plants, separated on a 1.4% agarose-formaldehyde gel and blotted onto nitrocellulose. The blot was hybridized with $^{32}P$-labeled CD127 insert. The difference in signal among samples is due to unequal loading of RNA as indicated by hybridizing the identical filter with a probe for ribulose bisphosphate carboxylase transcript. Markers are RNA ladder (Gibco BRL, Gaithersburg, Md.).

RNA blot analysis (FIG. 14) was used to determine if there were differences in transcript size or abundance produced by the CD127 family members among tomato lines resistant or susceptible to Pst. PolyA+RNA of Rio Grande-PtoR PtoR (Pto/Pto), Spectrum 151 (Pto/pto); and Moneymaker (pto/pto) was isolated from leaf tissue of 5 week-old plants, separated on a 1.4% agarose-formaldehyde gel and blotted into nitrocellulose. The blot was hybridized with $^{32}P$-labeled CD127 insert. A difference in abundance among the samples was mostly attributable to unequal loading of RNA as indicated by hybridizing the identical filter with a probe for ribulose bisphosphate carboxylase (Rubisco) transcript. (The Rubisco probe detects a gene transcript that is expected to be expressed equally in all tomato lines examined). A prominent 1.3 kb band was observed in resistant and susceptible lines. A fainter bank of 2.5 kb may indicate the presence of less abundant, longer transcripts in the CD127 family. No obvious induction of gene expression upon infection with Pst was observed. Thus, we could find no ifference in either abundance or transcript size and the basis of CD127 action is probably not due to a transcript of difference size being produced by the resistant line.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. An isolated gene fragment conferring bacterial disease resistance to plants by responding to an avirulence gene in bacterial plant pathogens, wherein said gene fragment encodes for a plant serine/threonine kinase.

2. An isolated gene fragment according claim 1, wherein said gene fragment encodes for the amino acid sequence corresponding to SEQ. ID. No. 1.

3. An isolated gene fragment according claim 2, wherein said gene fragment comprises the nucleotide sequence corresponding to SEQ. ID. No. 2.

4. An isolated gene fragment according to claim 2, wherein said gene fragment comprises the nucleotide sequence corresponding to SEQ. ID. No. 3.

5. An isolated gene fragment according claim 1, wherein said gene fragment imparts to tomato resistance to *Pseudomonas syringae*.

6. A recombinant DNA expression system comprising an expression vector into which is inserted a heterologous DNA conferring bacterial disease resistance to plants by responding to an avirulence gene in bacterial plant pathogens, wherein said DNA encodes for a plant serine/threonine kinase.

7. A recombinant DNA expression system according to claim 6, wherein said heterologous DNA encodes for the amino acid sequence corresponding to SEQ. ID. No. 1.

8. A recombinant DNA expression system according to claim 6, wherein said heterologous DNA is inserted into said vector in proper sense orientation and correct reading frame.

9. A recombinant DNA expression system according to claim 8, wherein said heterologous DNA comprises the nucleotide sequence corresponding to SEQ. ID. No. 2.

10. A recombinant DNA expression system according to claim 8, wherein said heterologous DNA comprises the nucleotide sequence corresponding to SEQ. ID. No. 3.

11. A cell transformed with a heterologous DNA conferring bacterial disease resistance to plants by responding to an avirulence gene in bacterial plant pathogens, wherein said heterologous DNA encodes for a plant serine/threonine kinase.

12. A cell according to claim 11, wherein said heterologous DNA encodes for the amino acid sequence corresponding to SEQ. ID. No. 1.

13. A cell according to claim 11, wherein said cell is selected from the group consisting of plant cells and bacteria.

14. A cell according to claim 13, wherein said cell is a plant cell selected from the group consisting of gymnosperm, monocot, and dicot.

15. A cell according to claim 14, wherein the host cell is a crop plant cell selected from the group consisting of rice, wheat, barley, rye, corn, potato, sweet potato, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum, and sugarcane.

16. A cell according to claim 13, wherein the cell is from the genus Agrobacterium.

17. A cell according to claim 11, wherein said heterologous DNA is inserted in a recombinant DNA expression system comprising an expression vector.

18. A transgenic plant transformed with a gene fragment conferring bacterial disease resistance to plants by responding to an avirulence gene in bacterial plant pathogens, wherein said gene fragment encodes for a plant serine/threonine kinase.

19. A transgenic plant according to claim 18, wherein said gene fragment encodes for the amino acid sequence corresponding to SEQ. ID. No. 1.

20. A transgenic plant according to claim 18, wherein said plant is selected from the group consisting of gymnosperm, monocot, and dicot.

21. A transgenic plant according to claim 20, wherein said plant is selected from the group consisting of rice, wheat, barley, rye, corn, potato, carrot, sweet potato, bean, pea, chicory, lettuce, cabbage, cauliflower, broccoli, turnip, radish, spinach, asparagus, onion, garlic, eggplant, pepper, celery, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum, and sugarcane.

22. A process of conferring disease resistance to plants comprising:

growing plant host cells transformed with a recombinant DNA expression system comprising an expression vector into which is inserted a heterologous DNA conferring bacterial disease resistance to plants by responding to an avirulence gene in bacterial plant pathogens, wherein said DNA encodes for a plant serine/threonine kinase; and expressing the heterologous DNA in the host cells to confer disease resistance on the host cells.

23. A process according to claim 22, wherein the heterologous DNA encodes for the amino acid sequence corresponding to SEQ. ID. No. 1.

24. A process according to claim 22, wherein the plant host cells are selected from the group consisting of gymnosperm, monocot, and dicot.

25. A process according to claim 24, wherein said plant host cells are selected from the group consisting of rice, wheat, barley, rye, corn, potato, carrot, sweet potato, bean, pea, chicory, lettuce, cabbage, cauliflower, broccoli, turnip, radish, spinach, asparagus, onion, garlic, eggplant, pepper, celery, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum, and sugarcane.

26. A process according to claim 22, wherein the plant host cells are transformed by a process comprising:

contacting the plant host cells with an inoculum of a bacterium from the genus Agrobacterium, wherein the bacterium is transformed with the recombinant DNA expression system.

27. A process according to claim 22, wherein the host cells are transformed by a process comprising:

propelling particles at the host cells under conditions effective for the particles to penetrate into the cell interior and introducing the recombinant DNA expression system into the cell interior.

28. A process according to claim 27, wherein the recombinant DNA expression system is carried into the cell interior together with the particles.

29. A process according to claim 27, wherein the recombinant DNA expression system surrounds the host cells and is drawn into the cell interior by the particle's wake.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 321 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:1:

```
Met Gly Ser Lys Tyr Ser Lys Ala Thr Asn Ser Ile Asn Asp Ala Leu
1               5                   10                  15

Ser Ser Ser Tyr Leu Val Pro Phe Glu Ser Tyr Arg Val Pro Leu Val
            20                  25                  30

Asp Leu Glu Glu Ala Thr Asn Asn Phe Asp His Lys Phe Leu Ile Gly
        35                  40                  45

His Gly Val Phe Gly Lys Val Tyr Lys Gly Val Leu Arg Asp Gly Ala
    50                  55                  60

Lys Val Ala Leu Lys Arg Arg Thr Pro Glu Ser Ser Gln Gly Ile Glu
65                  70                  75                  80

Glu Phe Glu Thr Glu Ile Glu Thr Leu Ser Phe Cys Arg His Pro His
                85                  90                  95

Leu Val Ser Leu Ile Gly Phe Cys Asp Glu Arg Asn Glu Met Ile Leu
            100                 105                 110

Ile Tyr Lys Tyr Met Glu Asn Gly Asn Leu Lys Arg His Leu Tyr Gly
        115                 120                 125

Ser Asp Leu Pro Thr Met Ser Met Ser Trp Glu Gln Arg Leu Glu Ile
    130                 135                 140

Cys Ile Gly Ala Ala Arg Gly Leu His Tyr Leu His Thr Arg Ala Ile
145                 150                 155                 160

Ile His Arg Asp Val Lys Ser Ile Asn Ile Leu Leu Asp Glu Asn Phe
                165                 170                 175

Val Pro Lys Ile Thr Asp Phe Gly Ile Ser Lys Lys Gly Thr Glu Leu
            180                 185                 190

Asp Gln Thr His Leu Ser Thr Val Val Lys Gly Thr Leu Gly Tyr Ile
        195                 200                 205

Asp Pro Glu Tyr Phe Ile Lys Gly Arg Leu Thr Glu Lys Ser Asp Val
    210                 215                 220

Tyr Ser Phe Gly Val Val Leu Phe Glu Val Leu Cys Ala Arg Ser Ala
225                 230                 235                 240

Ile Val Gln Ser Leu Pro Arg Glu Met Val Asn Leu Ala Glu Trp Ala
                245                 250                 255

Val Glu Ser His Asn Asn Gly Gln Leu Glu Gln Ile Val Asp Pro Asn
            260                 265                 270

Leu Ala Asp Lys Ile Arg Pro Glu Ser Leu Arg Lys Phe Gly Asp Thr
        275                 280                 285

Ala Val Lys Cys Leu Ala Leu Ser Ser Glu Asp Arg Pro Ser Met Gly
    290                 295                 300

Asp Val Leu Trp Lys Leu Glu Tyr Ala Leu Arg Leu Gln Glu Ser Val
305                 310                 315                 320
```

Ile ( 2 ) INFORMATION FOR SEQ ID NO:2:

( i ) SEQUENCE CHARACTERISTICS:
( A ) LENGTH: 966 base pairs
( B ) TYPE: nucleic acid
( C ) STRANDEDNESS: double
( D ) TOPOLOGY: unknown ( i i ) MOLECULE TYPE: DNA (genomic)

( x i ) SEQUENCE DESCRIPTION: SEQ ID NO:2:

```
ATGGGAAGCA AGTATTCTAA GGCAACAAAT TCCATAAATG ATGCTTTAAG CTCGAGTTAT    60
CTCGTTCCTT TTGAAAGTTA TCGAGTTCCT TTAGTAGATT TGGAGGAAGC AACTAATAAT   120
TTTGATCACA AGTTTTTAAT TGGACATGGT GTCTTTGGGA AGGTTTACAA GGGTGTTTTG   180
CGTGATGGAG CAAAGGTGGC CCTGAAAAGG CGTACACCTG AGTCCTCACA AGGTATTGAA   240
GAGTTCGAAA CAGAAATTGA GACTCTCTCA TTTTGCAGAC ATCCGCATCT GGTTTCATTG   300
ATAGGATTCT GTGATGAAAG AAATGAGATG ATTCTAATTT ATAAATACAT GGAGAATGGG   360
AACCTCAAGA GACATTTGTA TGGATCAGAT CTACCCACAA TGAGCATGAG CTGGGAGCAG   420
AGGCTGGAGA TATGCATAGG GGCAGCCAGA GGTCTACACT ACCTTCATAC TAGAGCAATT   480
ATACATCGTG ATGTCAAGTC TATAAACATA TTGCTTGATG AGAATTTTGT GCCAAAAATT   540
ACTGATTTTG GAATATCCAA GAAAGGGACT GAGCTTGATC AAACCCATCT TAGCACAGTA   600
GTGAAAGGAA CTCTCGGCTA CATTGACCCT GAATATTTTA TAAAGGGACG ACTCACTGAA   660
AAATCTGATG TTTATTCTTT CGGTGTTGTT TTATTCGAAG TTCTTTGTGC TAGGTCTGCC   720
ATAGTTCAAT CTCTTCCAAG GGAGATGGTT AATTTAGCTG AATGGGCAGT GGAGTCGCAT   780
AATAATGGAC AGTTGGAACA AATCGTAGAT CCCAATCTTG CAGATAAAAT AAGACCAGAG   840
TCCCTCAGGA AGTTTGGAGA TACAGCGGTA AAATGCTTAG CTTTGTCTAG TGAAGATAGG   900
CCATCAATGG GTGATGTGTT GTGGAAACTG GAGTATGCAC TTCGTCTCCA AGAGTCTGTT   960
ATTTAA                                                              966
```

( 2 ) INFORMATION FOR SEQ ID NO:3:

( i ) SEQUENCE CHARACTERISTICS:
( A ) LENGTH: 2443 base pairs
( B ) TYPE: nucleic acid
( C ) STRANDEDNESS: double
( D ) TOPOLOGY: unknown ( i i ) MOLECULE TYPE: DNA (genomic)

( x i ) SEQUENCE DESCRIPTION: SEQ ID NO:3:

```
GAATTCGGCA CGAGCTTAAA TAATGTTATT TGAAGGTTAT TAAGTTGTAC TCAAGTCTCA    60
ATCATGGGAA GCAAGTATTC TAAGGCAACA AATTCCATAA ATGATGCTTT AAGCTCGAGT   120
TATCTCGTTC CTTTTGAAAG TTATCGAGTT CCTTTAGTAG ATTTGGAGGA AGCAACTAAT   180
AATTTTGATC ACAAGTTTTT AATTGGACAT GGTGTCTTTG GGAAGGTTTA CAAGGGTGTT   240
TTGCGTGATG GAGCAAAGGT GGCCCTGAAA AGGCGTACAC CTGAGTCCTC ACAAGGTATT   300
GAAGAGTTCG AAACAGAAAT TGAGACTCTC TCATTTTGCA GACATCCGCA TCTGGTTTCA   360
TTGATAGGAT TCTGTGATGA AAGAAATGAG ATGATTCTAA TTTATAAATA CATGGAGAAT   420
GGGAACCTCA AGAGACATTT GTATGGATCA GATCTACCCA CAATGAGCAT GAGCTGGGAG   480
CAGAGGCTGG AGATATGCAT AGGGGCAGCC AGAGGTCTAC ACTACCTTCA TACTAGAGCA   540
```

-continued

ATTATACATC GTGATGTCAA GTCTATAAAC ATATTGCTTG ATGAGAATTT TGTGCCAAAA 600

ATTACTGATT TTGGAATATC CAAGAAAGGG ACTGAGCTTG ATCAAACCCA TCTTAGCACA 660

GTAGTGAAAG GAACTCTCGG CTACATTGAC CCTGAATATT TTATAAAGGG ACGACTCACT 720

GAAAAATCTG ATGTTTATTC TTTCGGTGTT GTTTTATTCG AAGTTCTTTG TGCTAGGTCT 780

GCCATAGTTC AATCTCTTCC AAGGGAGATG GTTAATTTAG CTGAATGGGC AGTGGAGTCG 840

CATAATAATG GACAGTTGGA ACAAATCGTA GATCCCAATC TTGCAGATAA AATAAGACCA 900

GAGTCCCTCA GGAAGTTTGG AGATACAGCG GTAAAATGCT TAGCTTTGTC TAGTGAAGAT 960

AGGCCATCAA TGGGTGATGT GTTGTGGAAA CTGGAGTATG CACTTCGTCT CCAAGAGTCT 1020

GTTATTTAAG ATATTTTTGT TTTTCTGAGT TTTATATAGA AAAAGGTAAA CTTTGAAAAC 1080

TTGAATTGCT ATACCTGTGG ATCCTTCTTT CATTTTATTA GGTGCGTCCG GCTGTTACAC 1140

ATATTGTATA TGGTTCTTAT TAAGTTCTTC AGACATTTTG TTATTGTAAA GAGGCAAAAA 1200

GGAAGTTTGC TGCTTTGACA TAGTCAATCT AAAACTATAT ACATTCAACT TTCAGAATGG 1260

AACTATAAAA GTTTGTGGAG CAATTCAAAA TGTTACTCAA CCTGTTCACA AAATGACTAT 1320

TGTAGAGCAA TAATGGTTAT AATATATAAC CATTATTGAG TAATATTTTT GTAGTAGTAT 1380

TGCCCAAGTC CATTAGCGGA GAGGTAATTT TCTTTTTGGT TCTCTCTTCC ACAATAGCTA 1440

TCAATCTCTC TGTCTTCTCG CTAAATTTCC TCAGTTGTGG TATAATCAGA GGTTCCTAAG 1500

CCTTCTGTTT TGTATACATA TATTTGTGAT TTTCATCTAT CATGCTTACT GTTAGGAGTT 1560

ATATTGCTTG ATGAGAATTT TGTGGCAAAA ATTAATGATT TTGGTCGATT CAAGAAGCTT 1620

GATCAAACCC ATGTTACCAC AATAGTAAAG GAACTTTTGG TTACCTTGAC CCTGAATATT 1680

ATCAAACTAG TCAGCTGACA GAAAAATCTG ATGTTTATTC TTTCGGTGTT GTTTTATTAG 1740

AAGTTATTTG TGCTAGGCCT GCGCTGGATT CATCTCGTTC GAGGGAGATG GTCAGCTCAG 1800

TTAAATGGGC AAAGGAGTGT CAGAAGAACG GACAGTCGGA ACGAATTATA GATCCCAATC 1860

TTGTTGGCAA AATAAGACCA GATTCCCCCA GGAAGTTTGG AGAAACAGCT GTGAAATGCT 1920

TAGCTGAAAC TGGCGTAAAC AGGCCATCAA TGGGTGAGGT GCTCGAGAAA CTGGACTATG 1980

CACTTCATCT CTAAGAGCCT GTCATTCAAG AAAACAGTAC CATCCCTATC CGCGAGCAAA 2040

TCAATGATTT CAGTCATGTT GATGACACTT CCTCTGCTTC TTCGGTCAAA ATTGGGCTGA 2100

TCTCTAGTAT GAATGCGTTC AGATTTTGCT CAAGAAAACA GCCGGGAGAA GTTCAATTAA 2160

TGGTTGCACT CCATGGGAAC CAACTATTCC AAGCCAACAA CTTCCATAAA TGATGCTTCC 2220

AATTTGAGTA ATCGCGTTCC TTTTGAAAGT TTTCGAGTTC CTTTTGTAGA TTTGCAGGAA 2280

GCAACTAATA ACTTTGATGA CAAGTTTCTG ATTGGAGTGG GTATATTTGG TAAGGATTAC 2340

AGGGGTGTTT TGCGTGATGG TACAAAGGTG GCCCTGAAAA GACATAAGCC TGAGTCTCCA 2400

CAAGGTATTG AAGAGTTCCG AACAGAAATC TCGTACCGAA TTC 2443

( 2 ) INFORMATION FOR SEQ ID NO:4:

( i ) SEQUENCE CHARACTERISTICS:
( A ) LENGTH: 23 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:4:

AAAGGAAGGT GGCTCCTACA AAT 23

-continued ( 2 ) INFORMATION FOR SEQ ID NO:5:

( i ) SEQUENCE CHARACTERISTICS:
( A ) LENGTH: 24 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:5:

```
CCTCTCCAAA TGAAATGAAC TTCC                                          24
```